United States Patent
Johnson

(10) Patent No.: US 8,171,611 B2
(45) Date of Patent: May 8, 2012

(54) METHOD FOR IMPLEMENTING A COMPONENT POSITIONING DEVICE

(75) Inventor: Stanley P. Johnson, Simsbury, CT (US)

(73) Assignee: Quest Metrology Group, LLC, Kent, WA (US)

( * ) Notice: Subject to any disclaimer, the term of this patent is extended or adjusted under 35 U.S.C. 154(b) by 1567 days.

(21) Appl. No.: 11/413,906

(22) Filed: Apr. 28, 2006

(65) Prior Publication Data

US 2007/0005165 A1    Jan. 4, 2007

Related U.S. Application Data

(62) Division of application No. 10/843,755, filed on May 12, 2004, now Pat. No. 7,128,298.

(51) Int. Cl.
*B23Q 17/22* (2006.01)
*B23Q 3/00* (2006.01)
*B23P 11/00* (2006.01)
*F16M 11/00* (2006.01)

(52) U.S. Cl. ... 29/407.09; 29/407.1; 29/464; 29/525.11; 29/559; 248/201; 248/694; 73/761

(58) Field of Classification Search ............... 29/407.09, 29/407.1, 428, 525.11, 559, 464; 248/201, 248/694, 542, 205.1, 200; 269/86; 73/865, 73/761

See application file for complete search history.

(56) References Cited

U.S. PATENT DOCUMENTS 5,619,783 A * 4/1997 Yasuhira et al. ........... 29/407.04

* cited by examiner

*Primary Examiner* — Jermie E Cozart

(57) ABSTRACT

A method for implementing a component positioning device is provided and includes obtaining a component, a component measuring device and a component positioning device, the component including a component head and a component base, the component measuring device including a first arbor and a second arbor and the component positioning device including a first support device, a second support device and an adapter device, connecting the first support device and the adapter device to the component measuring device, wherein the first support device is associated with the first arbor and the adapter device is associated with the second arbor, associating the second support device with the adapter device, wherein the second support device is adjacent to and separated from the first support device by a component cavity and positioning the component within the component cavity.

8 Claims, 27 Drawing Sheets

METHOD FOR IMPLEMENTING A COMPONENT POSITIONING DEVICE

RELATED APPLICATIONS

This application is a divisional application of U.S. Utility patent application Ser. No. 10/843,755 filed May 12, 2004, now U.S. Pat. No. 7,128,298 B1 which application is incorporated herein by reference in its entirety.

FIELD OF THE INVENTION

This disclosure relates generally to a component positioning device and more particularly to a component positioning device for use in an inspection system for inspecting the physical characteristics of threaded gages, screws, bolt and other components.

BACKGROUND OF THE INVENTION

As society becomes increasingly reliant upon technology, mechanical and electromechanical systems, such as aircraft, automobiles, weapons systems and power systems, are called upon to perform an ever increasing number of functions. One downside to this is that, in some situations, a failure of a single component in the system may cause a catastrophic failure of the entire system possibly resulting in the loss of millions of dollars and hundreds of lives. In an attempt to reduce the probability of a catastrophic systems failure, critical systems are required to satisfy predetermine operating tolerances before they may be used. As such, key components within these critical systems, i.e. components whose failure may cause a catastrophic system failure such as screws and/or gages, must also satisfy operating tolerances. If a component fails to satisfy these required design tolerances and/or performance specifications a degradation of system performance and/or a total system failure may occur.

One method of inspecting the physical characteristics of a component, such as the external threads of a screw, employs an attribute inspection approach that measures the physical characteristic of the component via a contact measurement technique. Unfortunately, these contact measurement techniques are time consuming and inaccurate, thus permitting non-conforming components to pass inspection. In response to the need for faster and more accurate component measurements, inspection systems that do not employ contact measurement techniques are being developed. One type of inspection system employs a vision inspection approach which visually captures an image of either an actual component or a silhouette of the component and determines the physical characteristics of the component from this image. However, in order to visually capture the image of a component, the component is disposed in a controlled manner using a component positioning device which is typically comprised of two rods or arbors, one of which may be spring loaded to hold the component in place by applying tension or pressure to the component.

Unfortunately, however, current component positioning devices have a plurality of disadvantages. First, these component positioning devices can only be used with components that have a straight geometry and as such, cannot be used with components that have bends or multiple branches, such as an elbow joint. Second, current designs of the component mount make it difficult to quickly center the component in between the mounting arbors.

Thus, there is a need for a component positioning device that can be used in an inspection system with a variety of components and that allows a component to be accurately and rapidly disposed for inspection.

SUMMARY OF THE INVENTION

A method for implementing a component positioning device is provided and includes obtaining a component, a component measuring device and a component positioning device, the component including a component head and a component base, the component measuring device including a first arbor and a second arbor and the component positioning device including a first support device, a second support device and an adapter device, connecting the first support device and the adapter device to the component measuring device, wherein the first support device is associated with the first arbor and the adapter device is associated with the second arbor, associating the second support device with the adapter device, wherein the second support device is adjacent to and separated from the first support device by a component cavity and positioning the component within the component cavity such that the component head is associated with one of the first support device and the second support device and the component base is associated with the other of the first support device and the second support device.

A medium encoded with a machine-readable computer program code, the program code including instructions for causing a controller to implement a method for implementing a component positioning device in a component measuring device, wherein the component measuring device includes a first arbor and a second arbor and the component positioning device includes a first support device, a second support device and an adapter device, the method including obtaining a component having a component head and a component base, connecting the first support device and the adapter device to the component measuring device, wherein the first support device is connected to the first arbor and the adapter device is connected to the second arbor, associating the second support device with the adapter device, wherein the second support device is adjacent to and separated from the first support device by a component cavity and positioning the component within the component cavity such that the component head is associated with one of the first support device and the second support device and the component base is associated with the other of the first support device and the second support device.

A machine-readable computer program code, the program code including instructions for causing a controller to implement a method for implementing a component positioning device in a component measuring device, wherein the component measuring device includes a first arbor and a second arbor and the component positioning device includes a first support device, a second support device and an adapter device, the method including obtaining a component having a component head and a component base, connecting the first support device and the adapter device to the component measuring device, wherein the first support device is connected to the first arbor and the adapter device is connected to the second arbor, associating the second support device with the adapter device, wherein the second support device is adjacent to and separated from the first support device by an component cavity and positioning the component within the component cavity such that the component head is associated with one of the first support device and the second support device and the component base is associated with the other of the first support device and the second support device.

The above discussed and other features and advantages of the present invention will be appreciated and understood by those skilled in the art from the following detailed description and drawings.

BRIEF DESCRIPTION OF THE DRAWING FIGURES

Referring to the exemplary drawings wherein like elements are numbered alike in the several Figures.

DETAILED DESCRIPTION OF THE INVENTION

Figure 1:
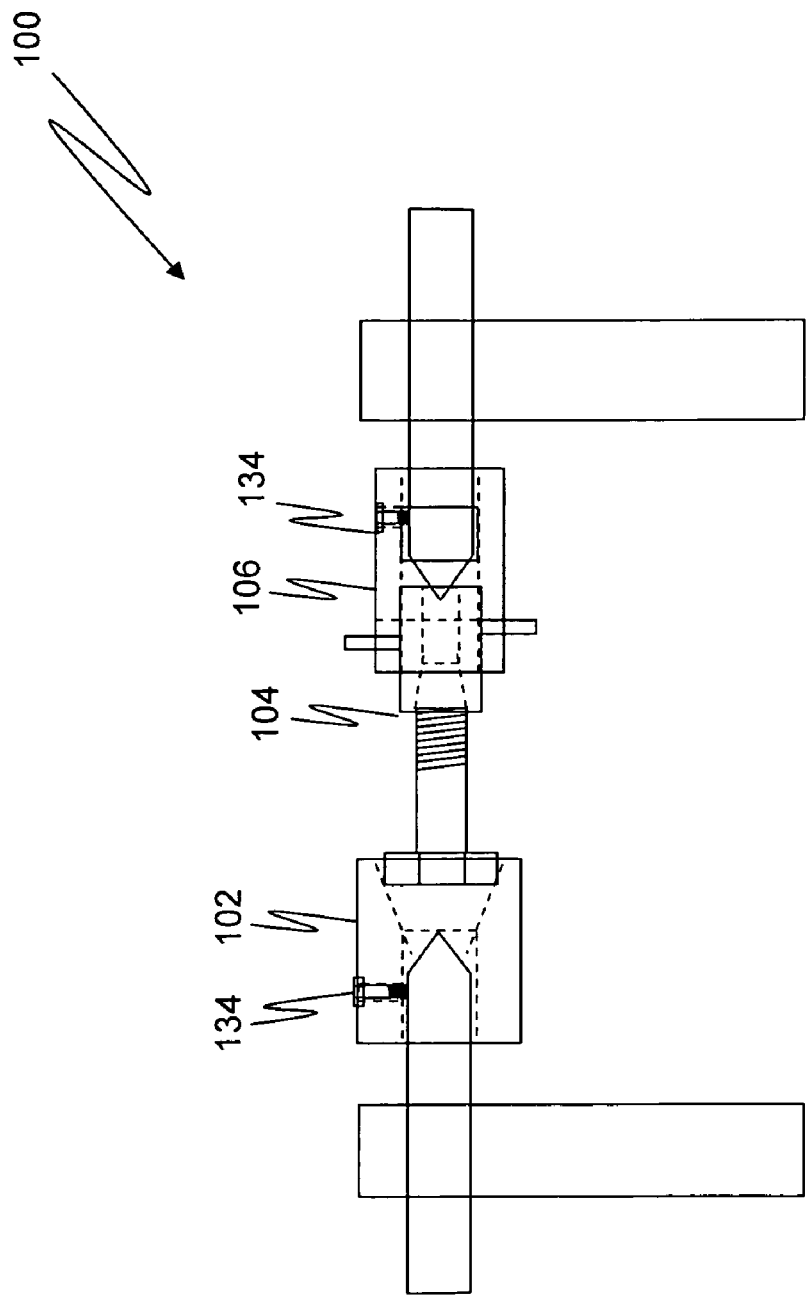
FIG. 1 is a side view of a component positioning device, in accordance with a first embodiment.
Figure 2:
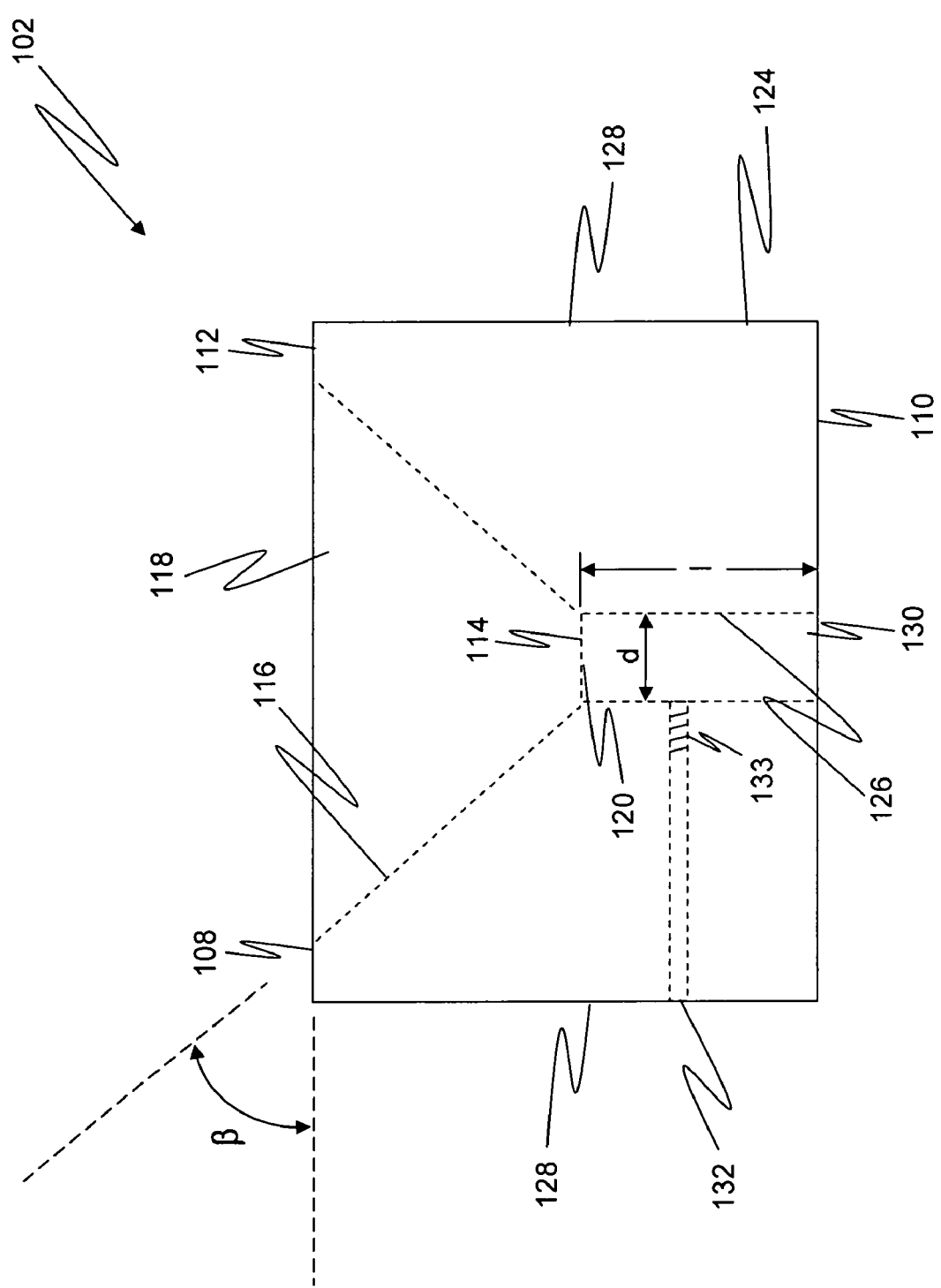
FIG. 2 is a cross sectional side view of a first support device, in accordance with a first embodiment.
Figure 3:
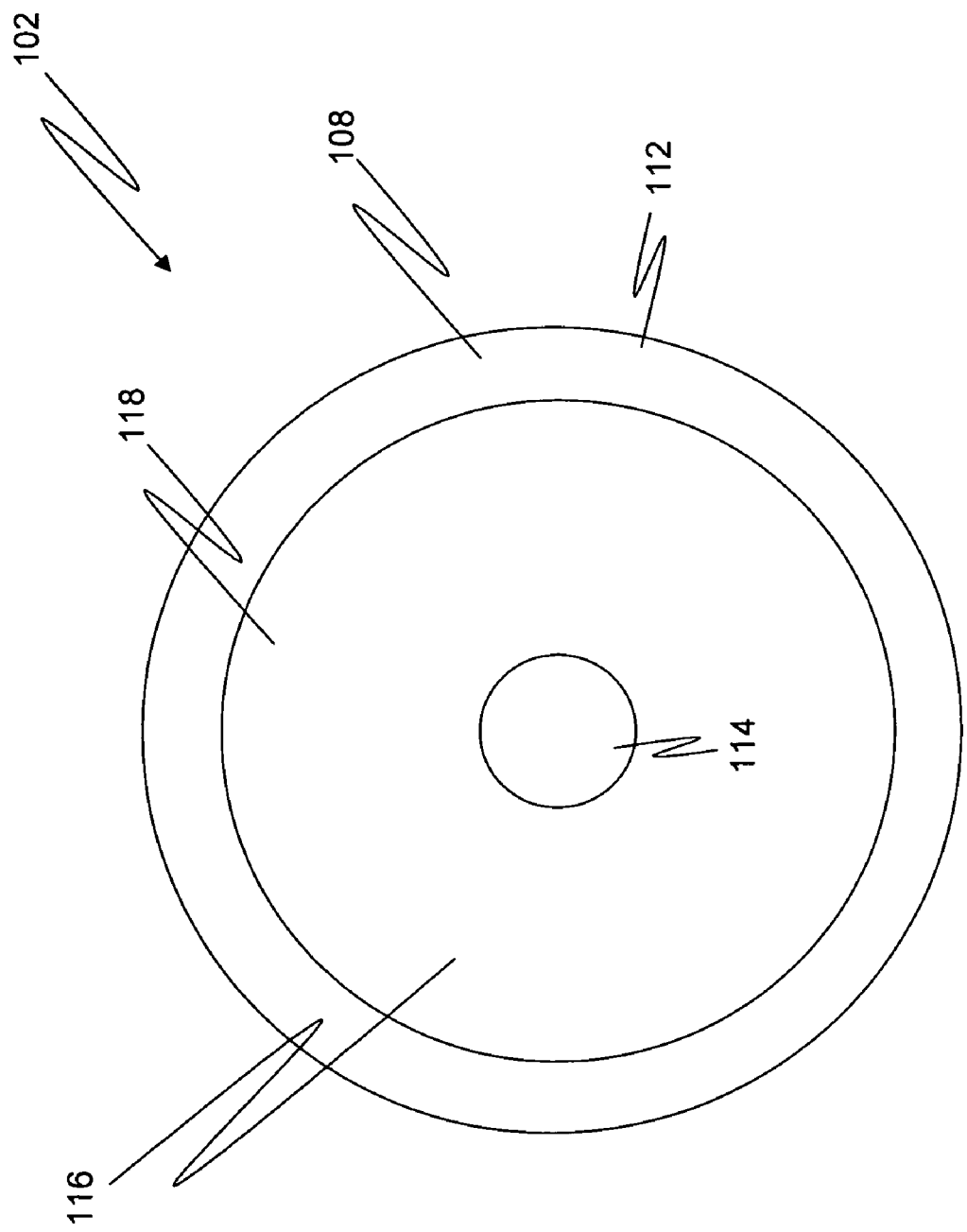
FIG. 3 is a top down view of a first support device, in accordance with a first embodiment.

Referring to FIG. 1, FIG. 2 and FIG. 3, a first embodiment of component positioning device 100 is shown wherein component positioning device 100 includes a first support device 102, a second support device 104 and an adapter device 106. First support device 102 includes a first upper portion 108 and a first lower portion 110. First upper portion 108 includes a first upper portion top 112, a first upper portion bottom 1 14 and a first upper portion cradle wall 116, wherein first upper portion cradle wall 116 extends from first upper portion top 112 to first upper portion bottom 114 at a first predetermined cradle angle β to define a conically shaped first component cradle 118. First lower portion 110 includes a first lower portion top 120, a first lower portion bottom 122 and a first lower portion wall 124 having a first lower portion inner surface 126 and a first lower portion outer surface 128, wherein first lower portion wall 124 defines a first arbor cavity 130 and a first fastening cavity 132.

First arbor cavity 130 includes a first arbor cavity diameter d and a first arbor cavity length l and first fastening cavity 132 may be disposed in the side of first lower portion wall 124 to communicate first lower portion outer surface 128 with first lower portion inner surface 126. Additionally, first fastening cavity 132 may include a threaded portion 133 for threadingly interacting with a threaded mounting screw 134. Although first arbor cavity 130 is shown as extending the length l of first lower portion 110, it should be appreciated that first arbor cavity 130 may extend only a portion of length l of first lower portion 110. It should be further appreciated that first upper portion 108 and/or conically shaped first component cradle 118 may be sized to accommodate components of varying sizes. Moreover, although first predetermined cradle angle β is shown as being at least 60° from horizontal, first predetermined cradle angle β may be any angle suitable to the desired end purpose, such as 45° and 75°.

Figure 4:
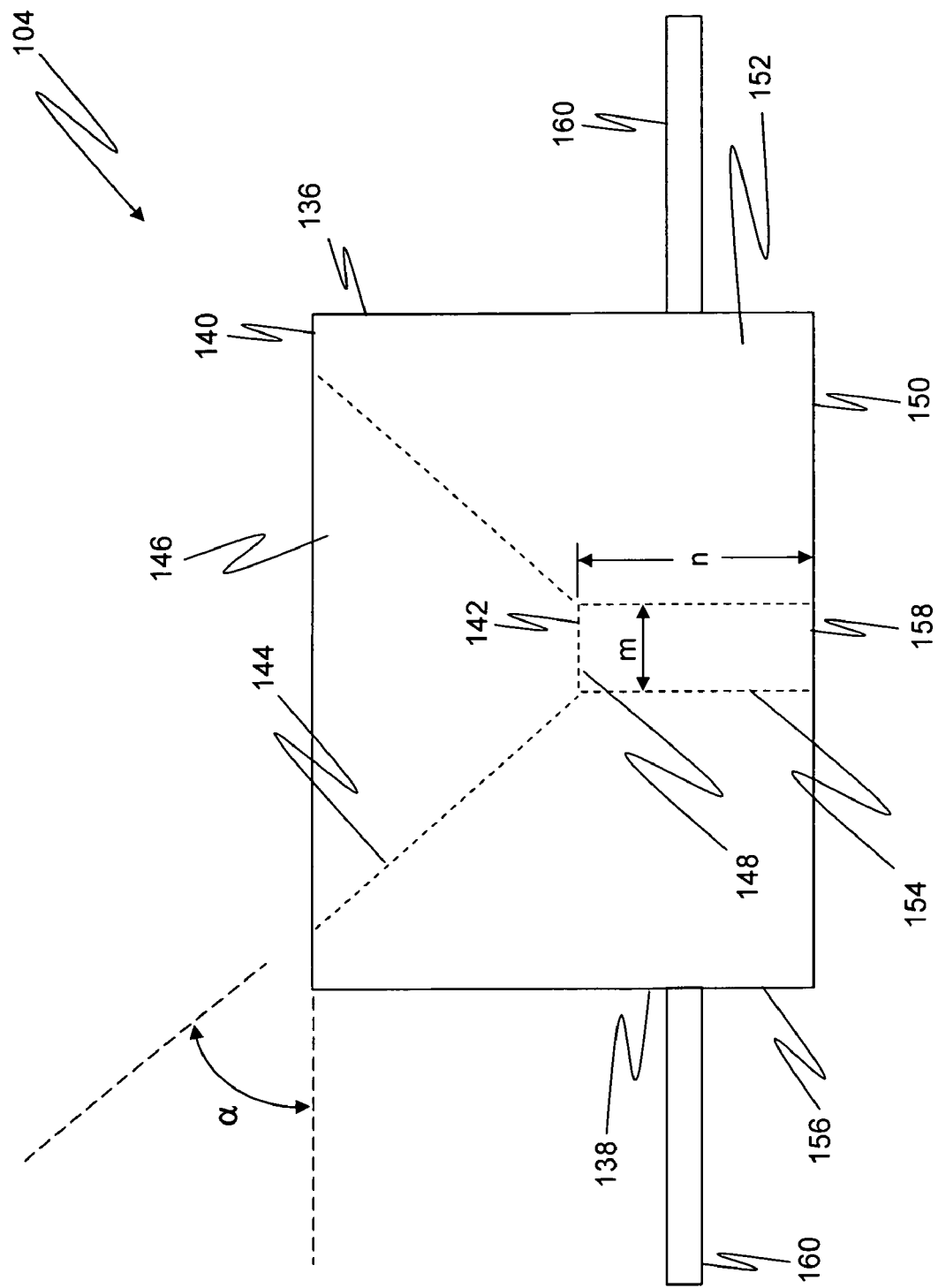
FIG. 4 is a cross sectional side view of a second support device, in accordance with a first embodiment.
Figure 5:
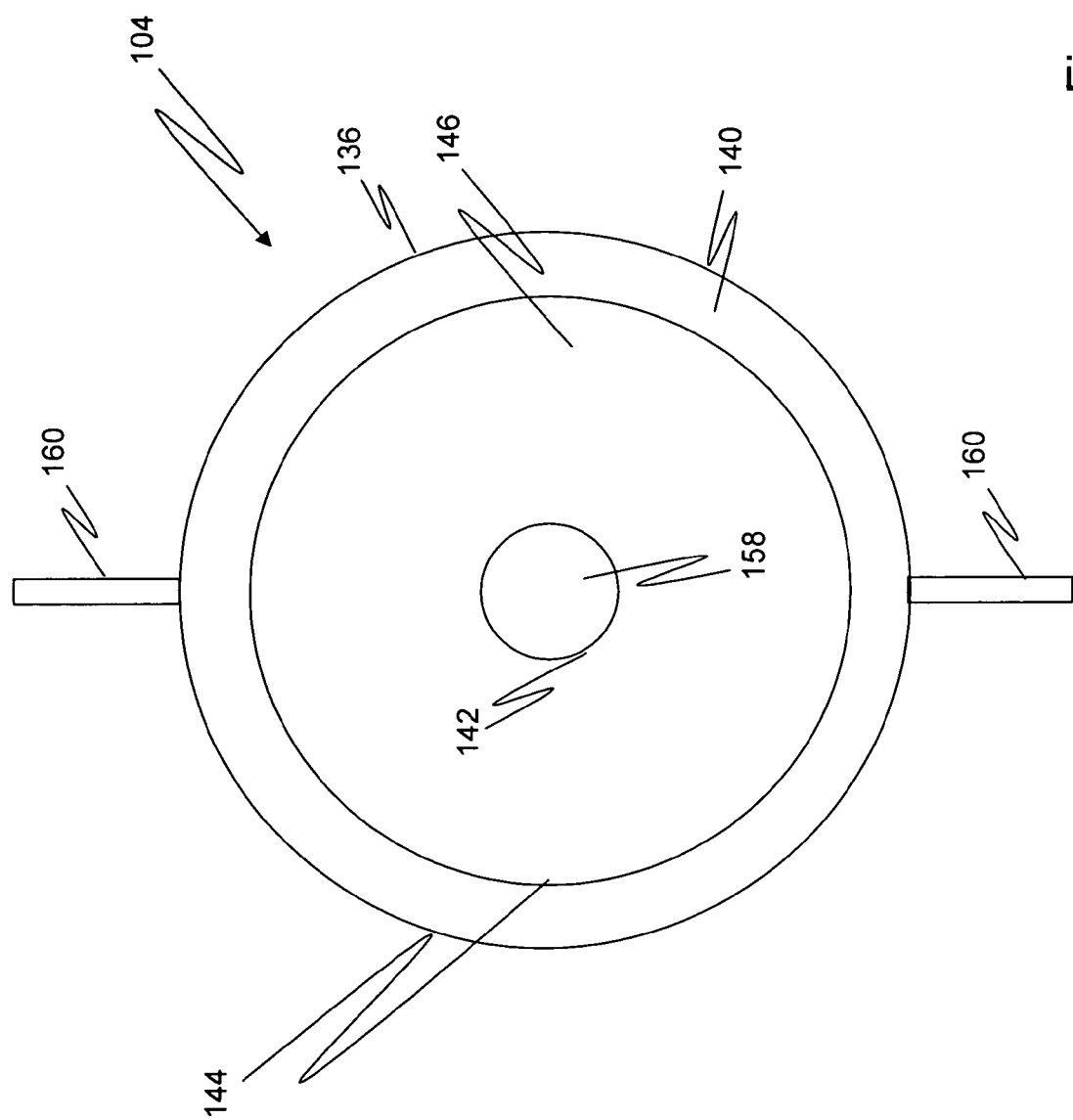
FIG. 5 is a top down view of a second support device, in accordance with a first embodiment.

Referring to FIG. 4 and FIG. 5, second support device 104 is shown and includes a second upper portion 136 and a second lower portion 138. Second upper portion 136 includes a second upper portion top 140, a second upper portion bottom 142 and a second upper portion cradle wall 144 extending from second upper portion top 140 to second upper portion bottom 142 at a second predetermined cradle angle α to define a conically shaped second component cradle 146. Second lower portion 138 includes a second lower portion top 148, a second lower portion bottom 150 and a second lower portion wall 152 having a second lower portion inner surface 154 and a second lower portion outer surface 156, wherein second lower portion wall 152 defines a second arbor cavity 158. Second lower portion 138 also includes at least one stabilizing member 160 protruding from second lower portion outer surface 156 and second arbor cavity 158 may include a second arbor cavity diameter m and a second arbor cavity length n.

Figure 6:
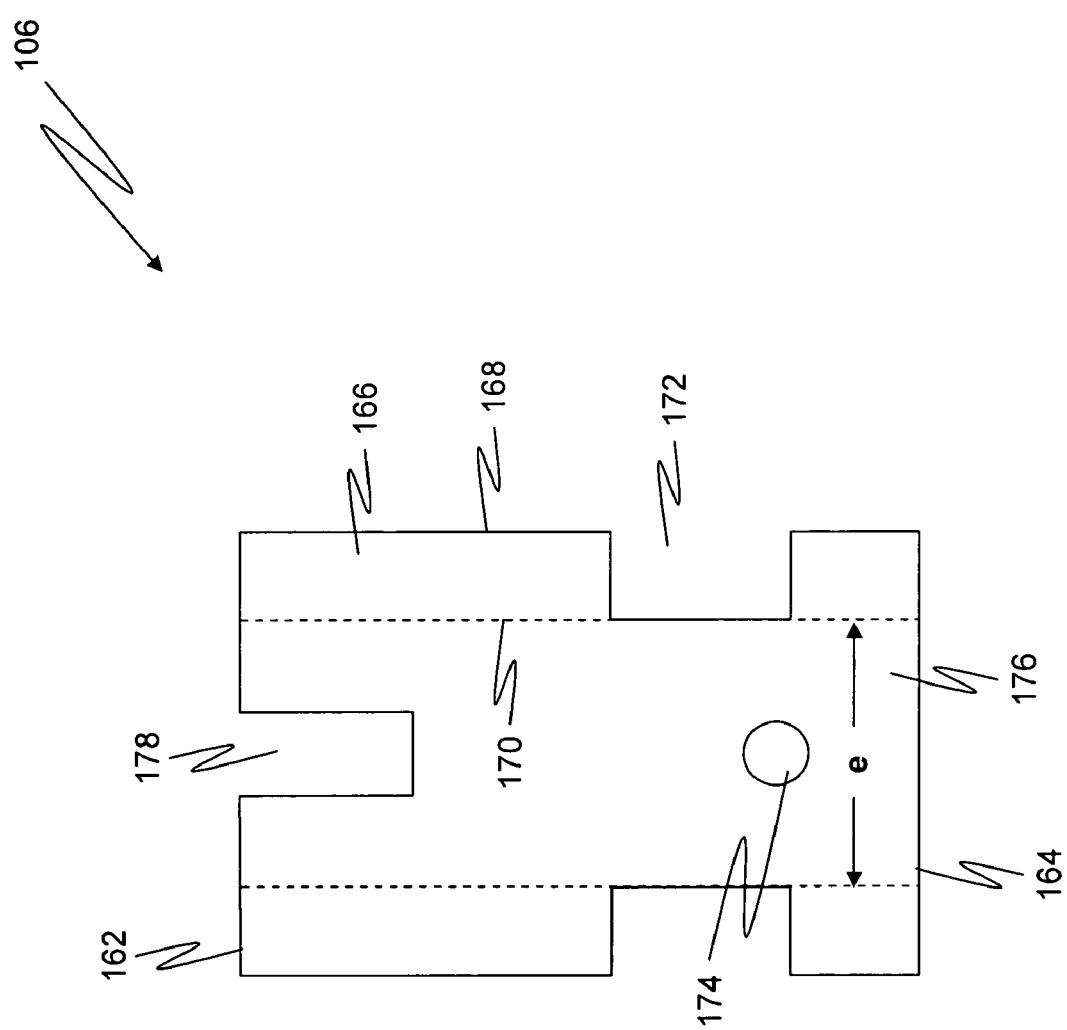
FIG. 6 is a cross sectional front view of an adapter device, in accordance with a first embodiment.
Figure 7:
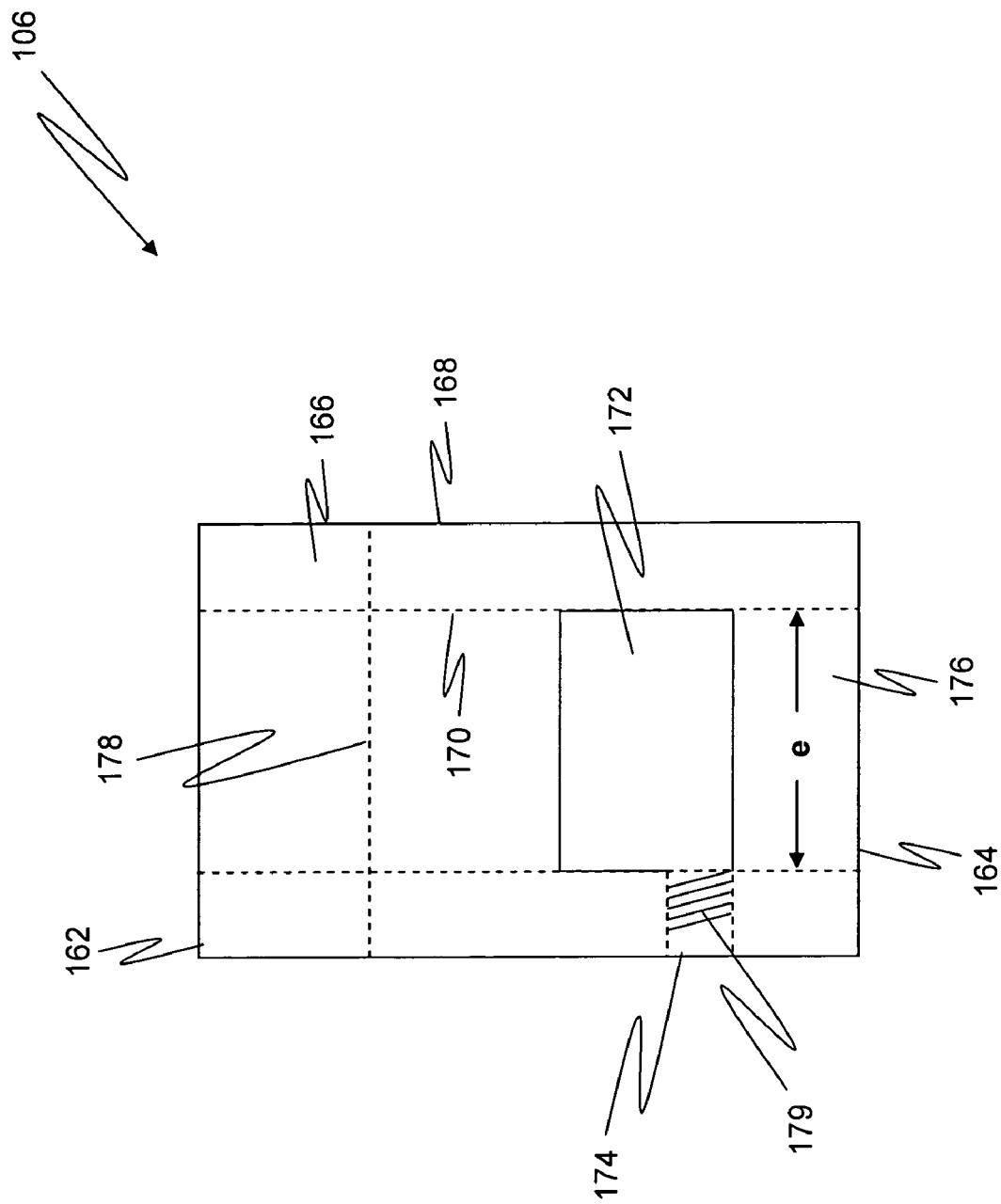
FIG. 7 is a cross sectional side view of an adapter device, in accordance with a first embodiment.

Referring to FIG. 6 and FIG. 7, adapter device 106 is shown and includes an adapter top 162, an adapter bottom 164 and an adapter wall 166, wherein adapter wall 166 includes an adapter outer wall 168, an adapter inner wall 170 and defines an adapter device cavity 172, an adapter fastening cavity 174, an adapter arbor cavity 176 and an adapter notch cavity 178. Adapter arbor cavity 176 may include a first arbor cavity diameter e and adapter fastening cavity 174 is disposed in the side of adapter wall 166 to communicate adapter outer wall 168 with adapter inner wall 170. Additionally, adapter device cavity 172 may be disposed in the side of adapter wall 166 to communicate adapter outer wall 168 with adapter inner wall 170. Moreover, adapter fastening cavity 174 may include a threaded portion 179 for receiving a threaded mounting screw 134. It should be appreciated that adapter device cavity 172 is sized, shaped and disposed in adapter wall 166 such that a reference mark on an arbor disposed within adapter arbor cavity 176 is in the line-of-sight of component measuring device 137.

Figure 8:
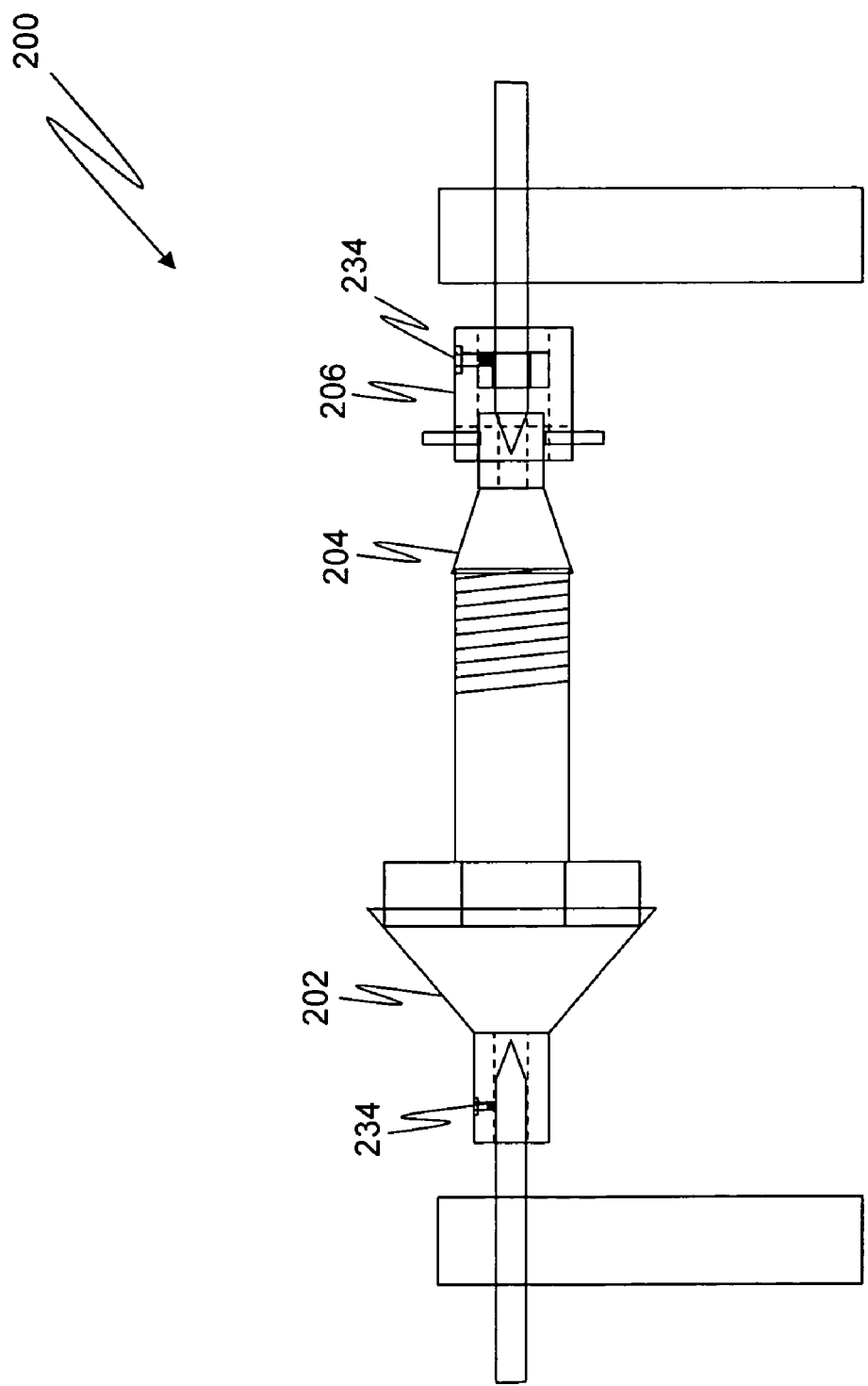
FIG. 8 is a side view of a component positioning device, in accordance with a second embodiment.
Figure 9:
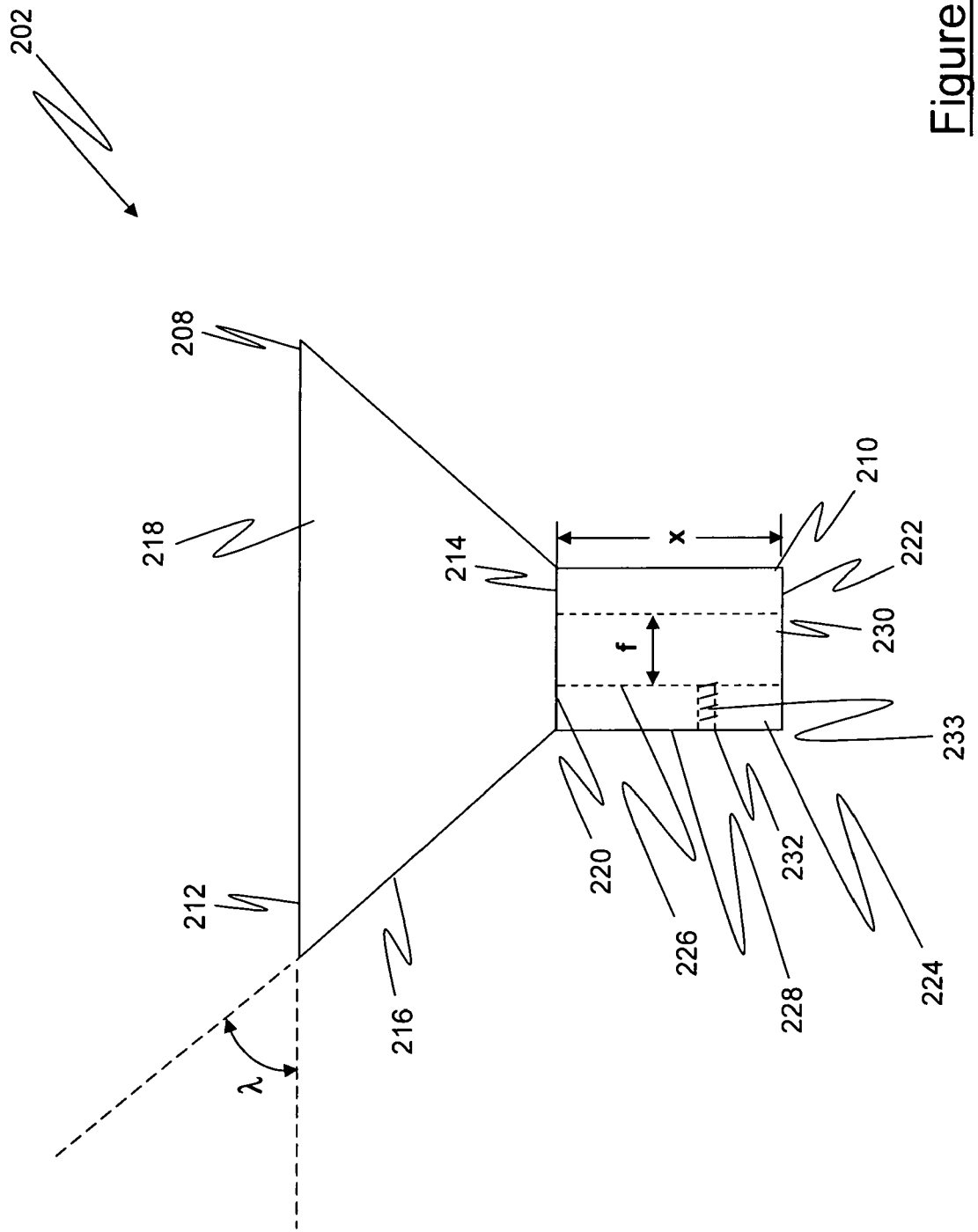
FIG. 9 is a cross sectional side view of a first support device, in accordance with a second embodiment.
Figure 10:
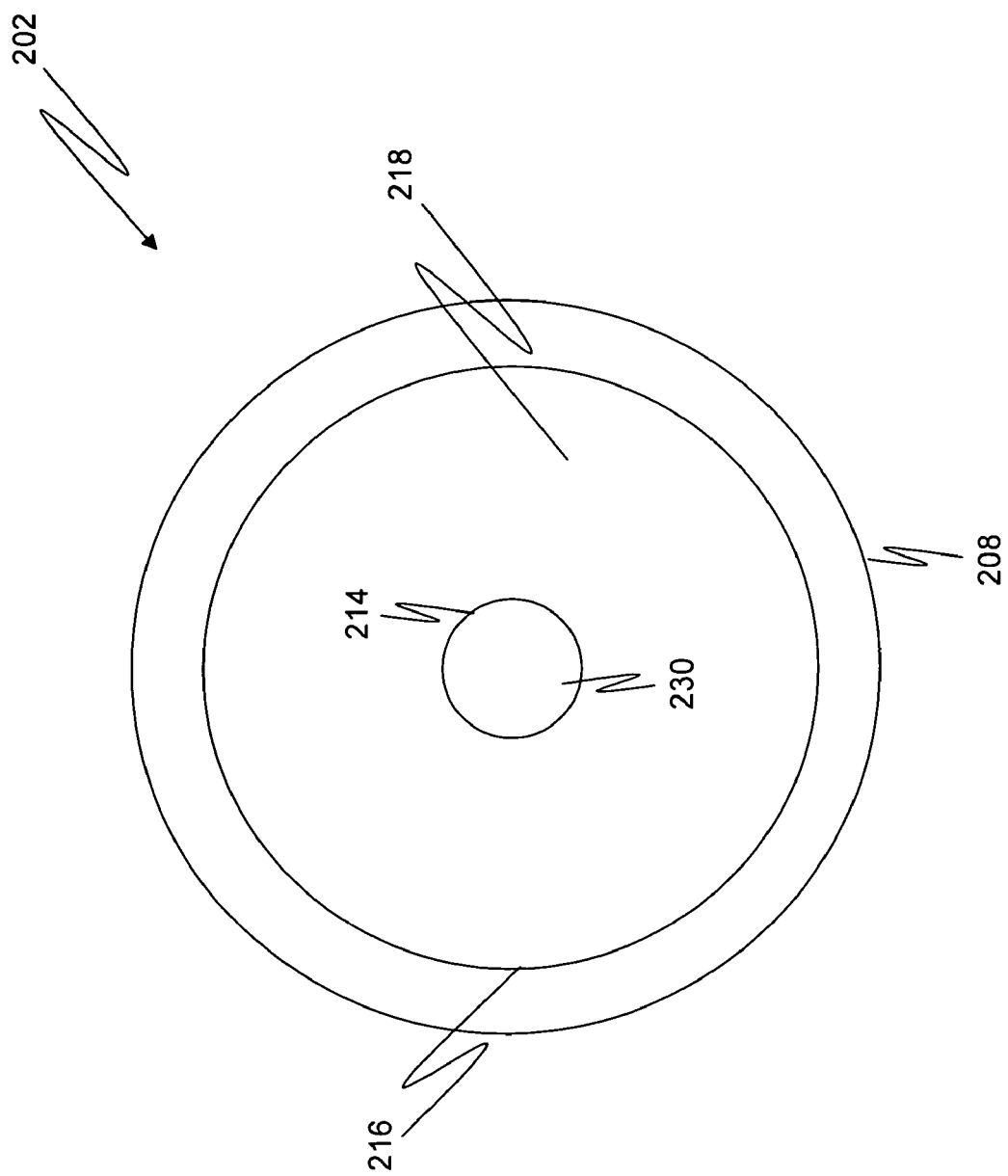
FIG. 10 is a top down view of a first support device, in accordance with a second embodiment.

Referring to FIG. 8, FIG. 9 and FIG. 10, a component positioning device 200 in accordance with a second embodiment is shown and discussed, wherein component positioning device 200 includes a first support device 202, a second support device 204 and an adapter device 206. First support device 202 includes a first upper portion 208 and a first lower portion 210. First upper portion 208 includes a first upper portion top 212, a first upper portion bottom 214 and a first upper portion cradle wall 216, wherein first upper portion cradle wall 216 extends from first upper portion top 212 to first upper portion bottom 214 at a first predetermined cradle angle $\lambda$ to define a conically shaped first component cradle 218. First lower portion 210 includes a first lower portion top 220, a first lower portion bottom 222 and a first lower portion wall 224 having a first lower portion inner surface 226 and a first lower portion outer surface 228, wherein first lower portion wall 224 defines a first arbor cavity 230 and a first fastening cavity 232.

First arbor cavity 230 includes a first arbor cavity diameter f and a first arbor cavity length x and first fastening cavity 232 may be disposed in the side of first lower portion wall 224 to communicate first lower portion outer surface 228 with first lower portion inner surface 226. Additionally, first fastening cavity 232 may include a threaded portion 233 for receiving a threaded mounting screw 234. Although first arbor cavity 230 is shown as extending the length of first lower portion 210, it is contemplated that first arbor cavity 230 may only extend a portion of the length of first lower portion 210. It is further contemplated that first upper portion 208 and/or conically shaped first component cradle 218 may be sized to accommodate components of varying sizes. Moreover, although it is contemplated that first predetermined cradle angle $\lambda$ is shown as being at least 60° from horizontal, first predetermined cradle angle $\lambda$ may be any angle suitable to the desired end purpose, such as 45° and 75°.

Figure 11:
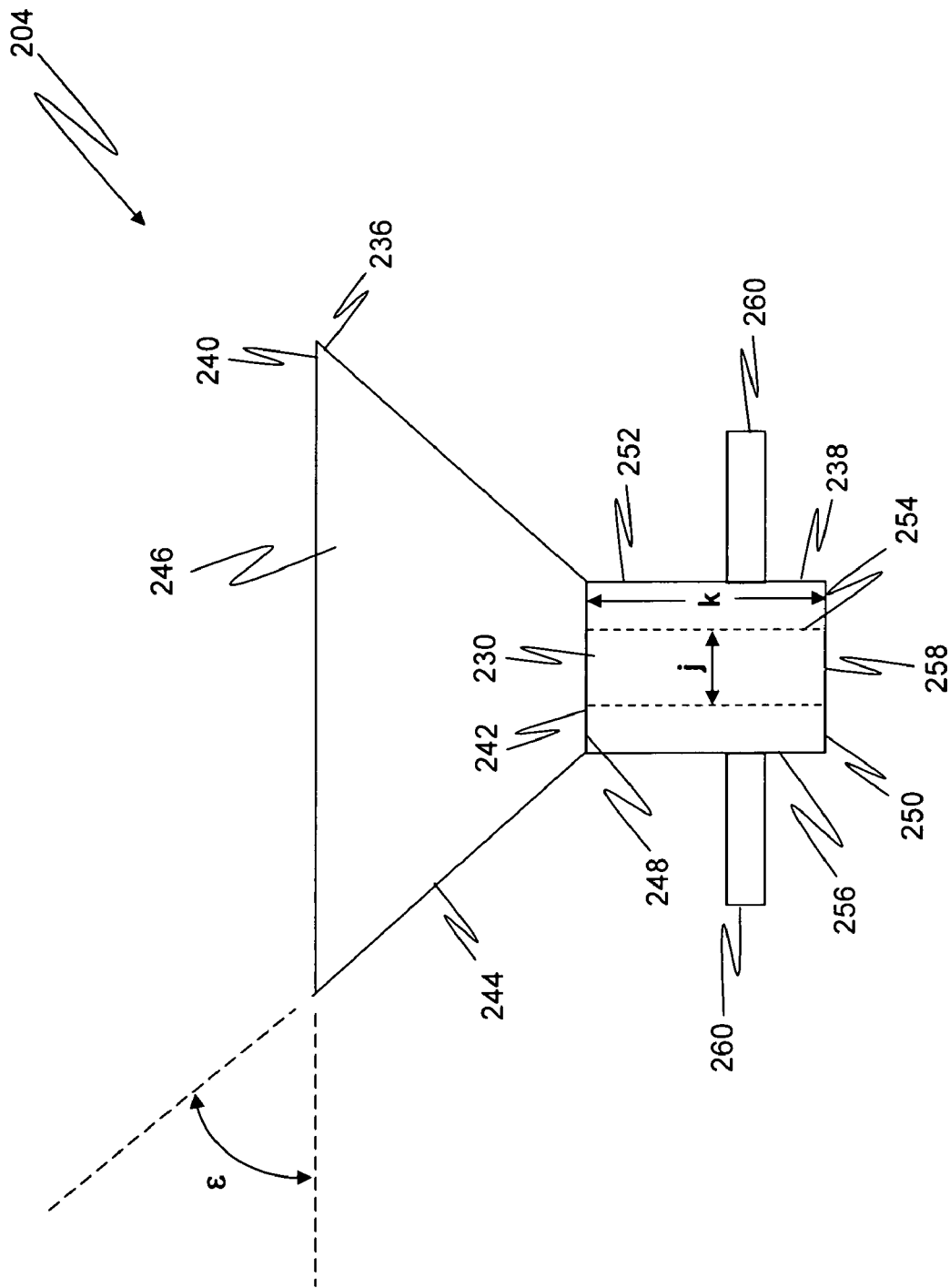
FIG. 11 is a cross sectional side view of a second support device, in accordance with a second embodiment.
Figure 12:
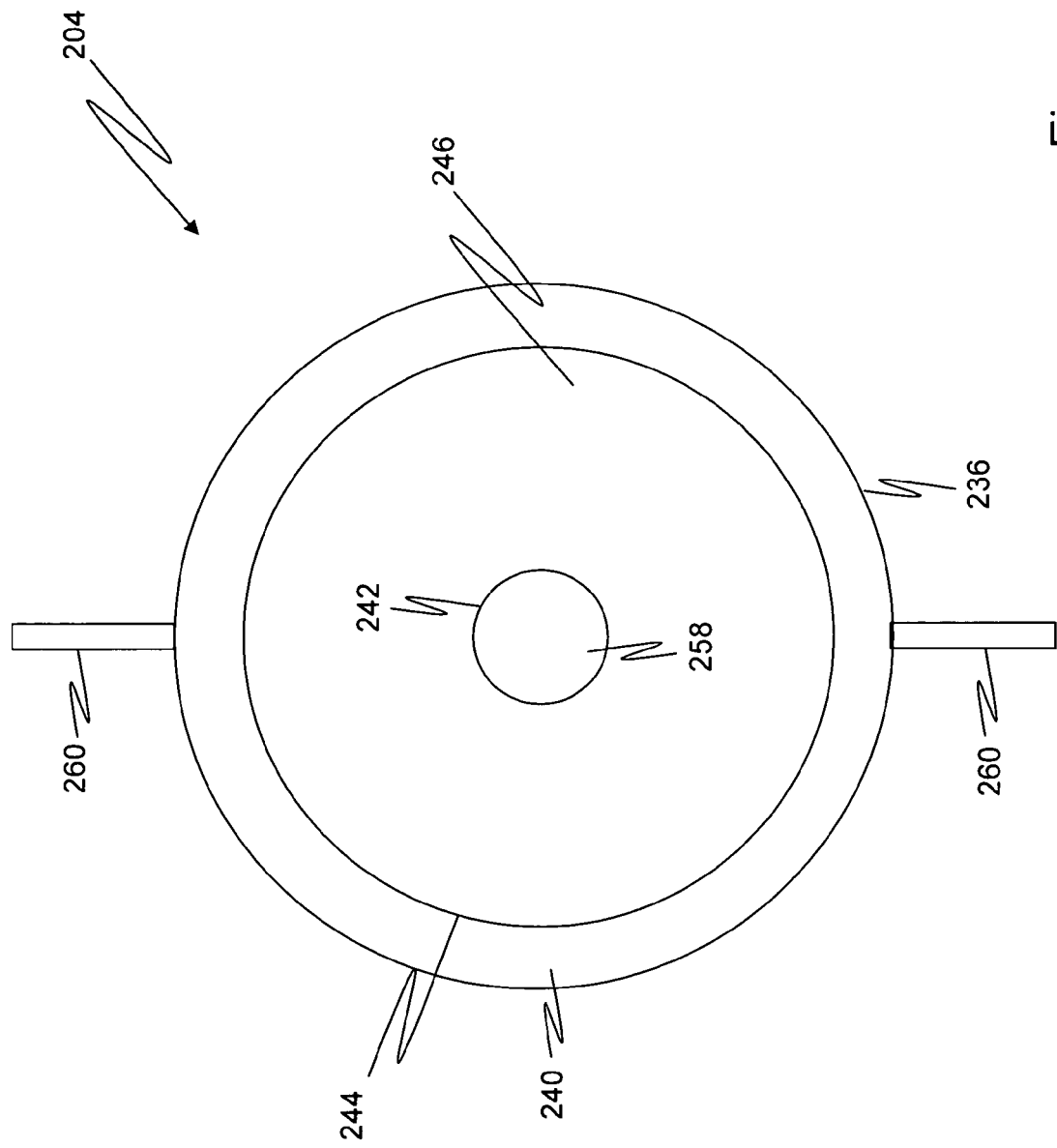
FIG. 12 is a top down view of a second support device, in accordance with a second embodiment.
Figure 13:
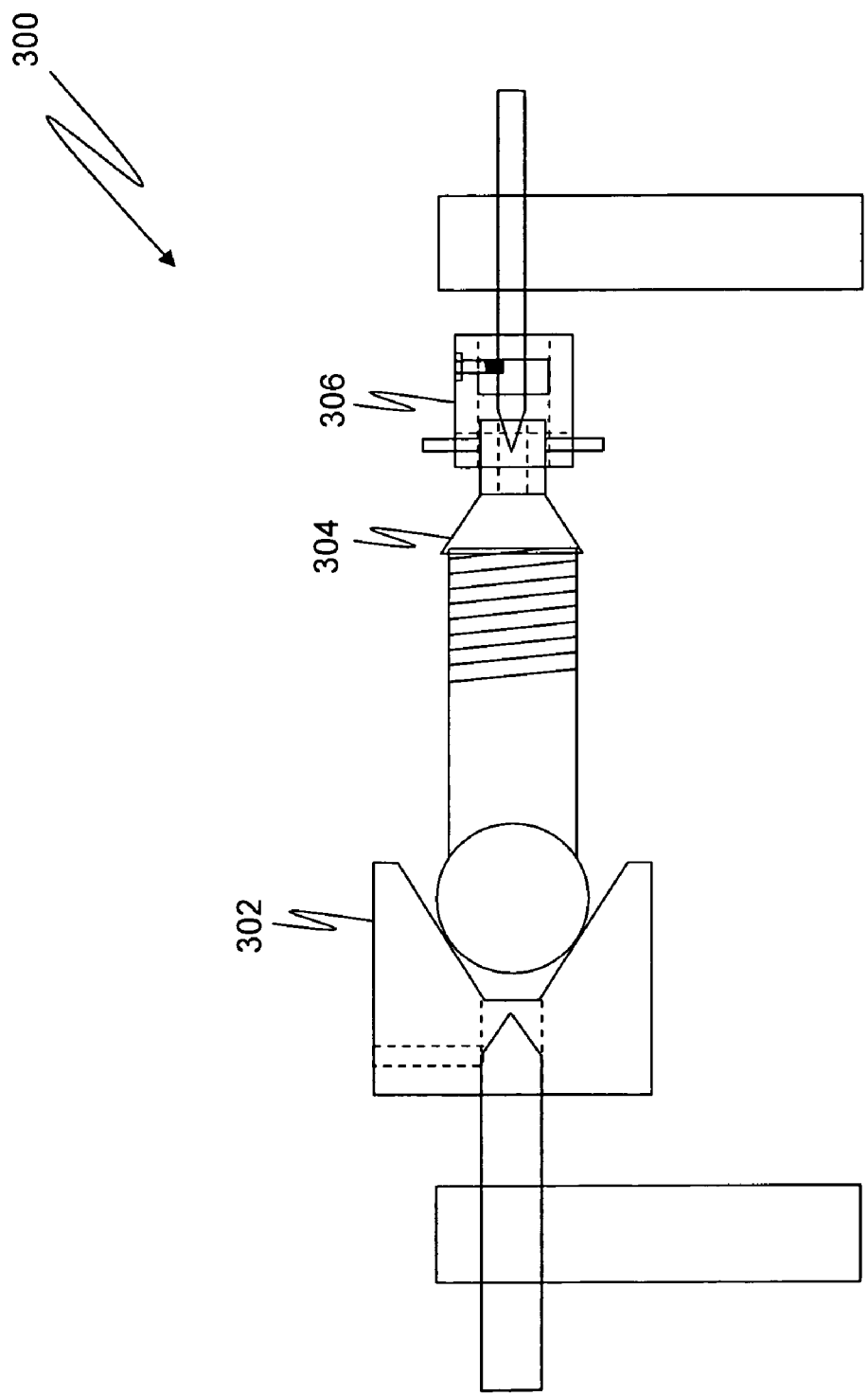
FIG. 13 is a side view of a component positioning device, in accordance with a fourth embodiment.
Figure 14:
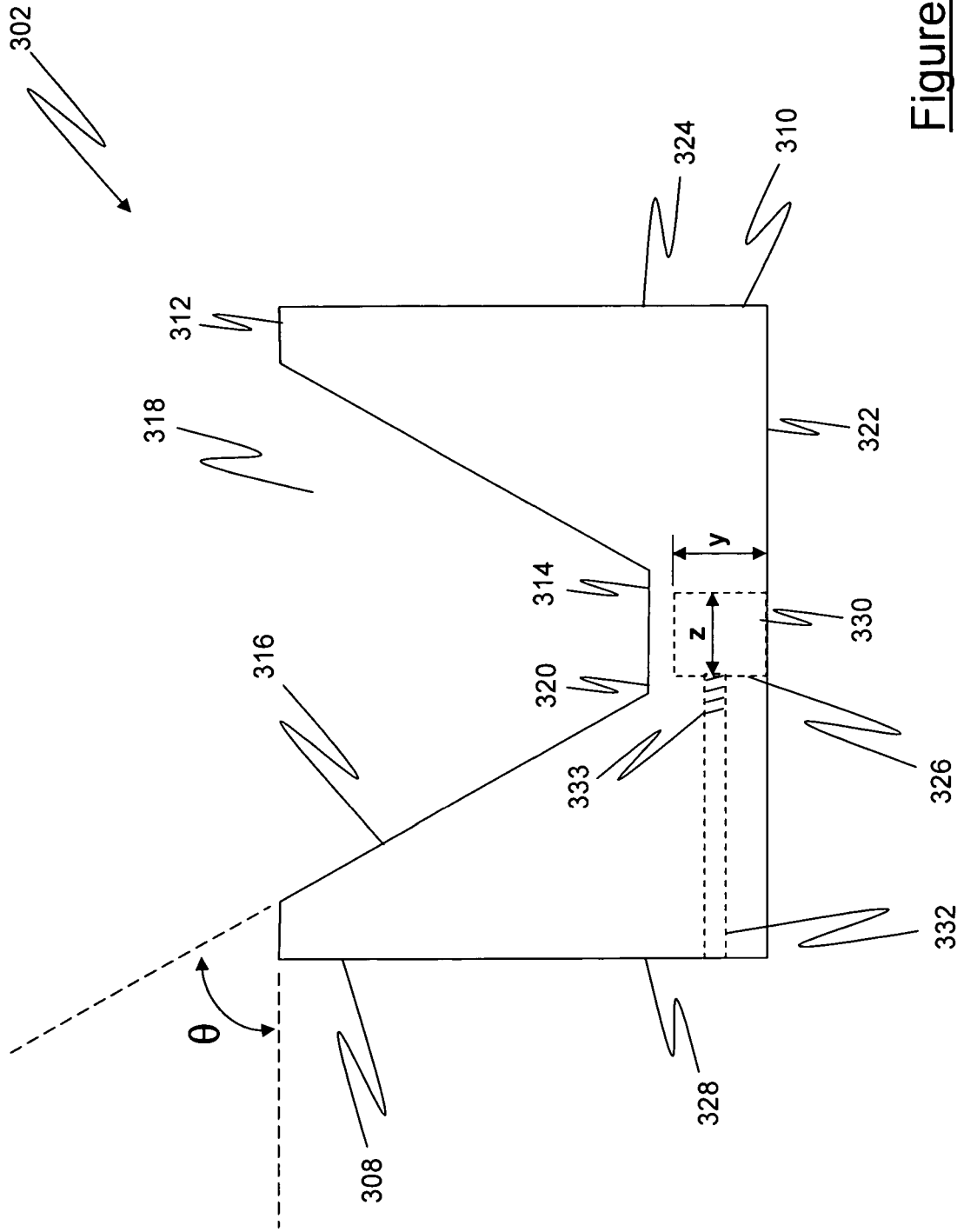
FIG. 14 is a cross sectional side view of a first support device, in accordance with a fourth embodiment.
Figure 15:
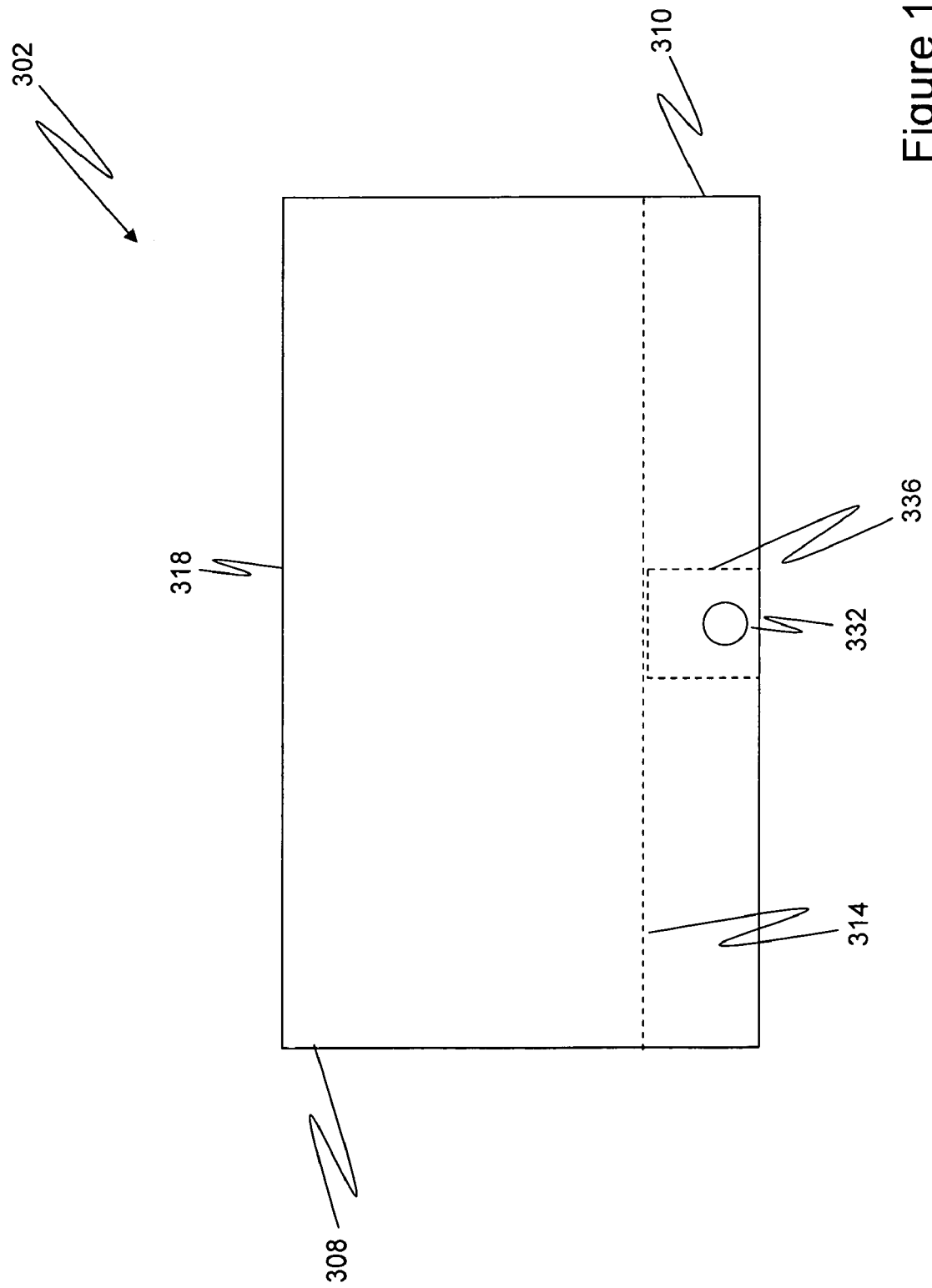
FIG. 15 is a cross sectional side view of a first support device, in accordance with a fourth embodiment.
Figure 16:
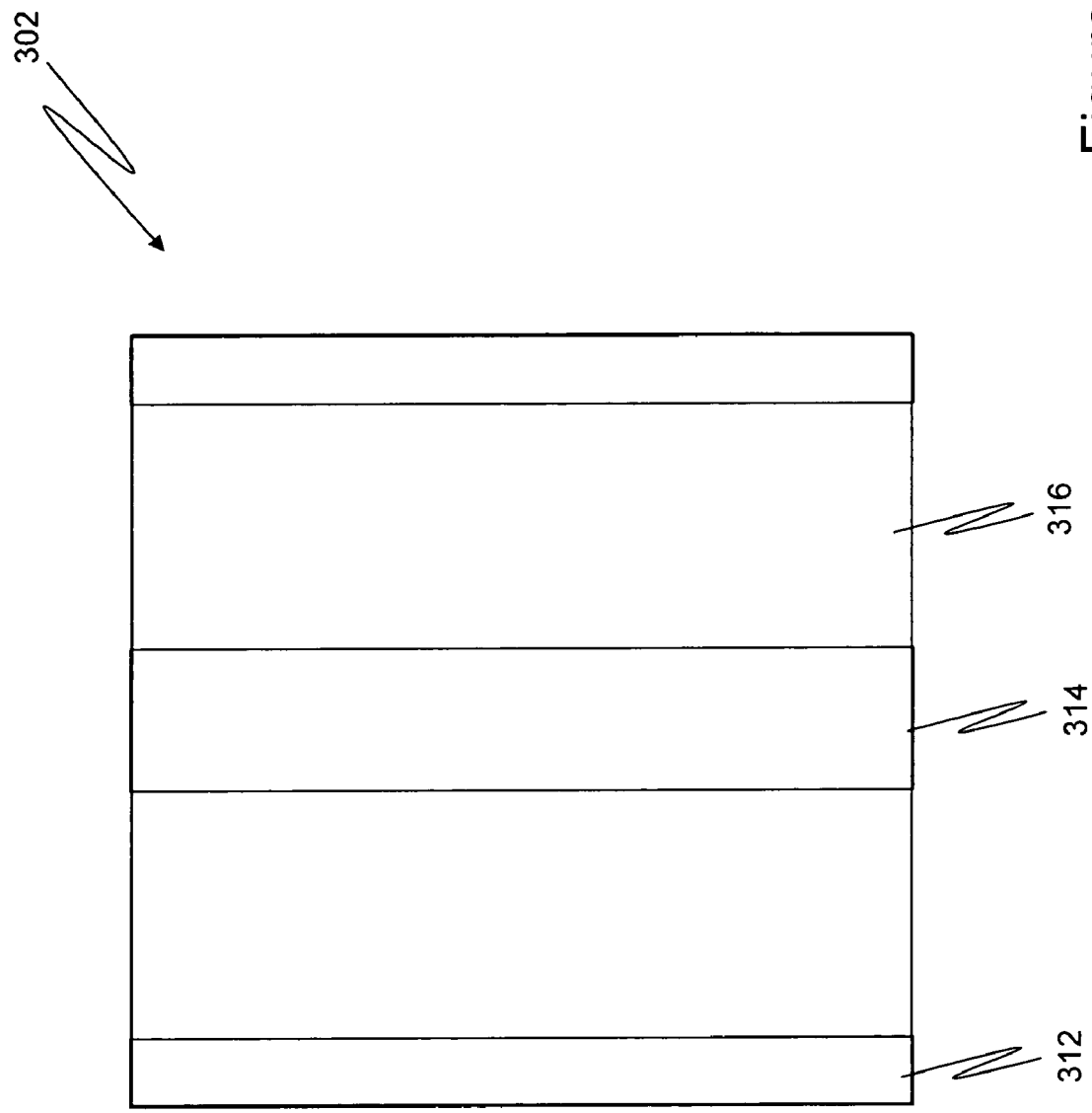
FIG. 16 is a top down view of a first support device, in accordance with a fourth embodiment.

Referring to FIG. 11 and FIG. 12, second support device 204 is shown and includes a second upper portion 236 and a second lower portion 238. Second upper portion 236 includes a second upper portion top 240, a second upper portion bottom 242 and a second upper portion cradle wall 244 extending from second upper portion top 240 to second upper portion bottom 242 at a second predetermined cradle angle $\epsilon$ to define a conically shaped second component cradle 246. Second lower portion 238 includes a second lower portion top 248, a second lower portion bottom 250 and a second lower portion wall 252 having a second lower portion inner surface 254 and a second lower portion outer surface 256, wherein second lower portion wall 252 defines a second arbor cavity 258. Second lower portion 238 also includes at least one stabilizing member 260 protruding out of and away from second lower portion outer surface 256 and second arbor cavity 258 may include a second arbor cavity diameter j and a second arbor cavity length k. It is contemplated that second upper portion 236 and/or conically shaped second component cradle 246 may be sized to accommodate components of varying sizes. Moreover, although second predetermined cradle angle $\epsilon$ is shown as being at least 60° from horizontal, second predetermined cradle angle $\epsilon$ may be any angle suitable to the desired end purpose, such as 45° and 75°. It is further contemplated that adapter device 206 may be any adapter device suitable to the desired end purpose, such as adapter device 106.

Referring to FIG. 13, FIG. 14, FIG. 15 and FIG. 16, a component positioning device 300 in accordance with a third embodiment is shown and discussed, wherein component positioning device 300 includes a first support device 302, a second support device 304 and an adapter device 306. First support device 302 includes a first upper portion 308 and a first lower portion 310. First upper portion 308 includes a first upper portion top 312, a first upper portion bottom 314 and a first upper portion cradle wall 316, wherein first upper portion cradle wall 316 extends from first upper portion top 312 to first upper portion bottom 314 at a first predetermined cradle angle $\theta$ to define a substantially rectangular shaped first component cradle 318. First lower portion 310 includes a first lower portion top 320, a first lower portion bottom 322 and a first lower portion wall 324 having a first lower portion inner surface 326 and a first lower portion outer surface 328, wherein first lower portion wall 324 defines a first arbor cavity 330 and a first fastening cavity 332.

First arbor cavity 330 includes a first arbor cavity diameter z and a first arbor cavity length y and first fastening cavity 332 may be disposed in the side of first lower portion wall 324 to communicate first lower portion outer surface 328 with first lower portion inner surface 326. Additionally, first fastening cavity 332 may include a threaded portion 333 for threadingly interacting with a threaded mounting screw 334. Although first arbor cavity 330 is shown as extending the length of first lower portion 310, it is contemplated that first arbor cavity 330 may extend only a portion of the length of first lower portion 310. It is further contemplated that first upper portion 308, substantially rectangular shaped first component cradle 318 and first predetermined cradle angle $\theta$ may be sized to accommodate components of varying sizes.

It should be appreciated that first upper portion 308 and/or substantially rectangular shaped first component cradle 318 may be sized to accommodate components of varying sizes. Moreover, although first predetermined cradle angle $\theta$ is shown as being at least 60° from horizontal, first predetermined cradle angle $\theta$ may be any angle suitable to the desired end purpose, such as 45° and 75°. Additionally, second support device 304 may be any support device suitable to the desired end purpose, such as second support device 204 and second support device 104. Furthermore, adapter device 306 may be any adapter device suitable to the desired end purpose, such as adapter device 106.

Referring to FIGS. 17-23, a block diagram illustrating a method 400 for implementing a component positioning device 100, 200 is shown and discussed. A component positioning device 100, 200, a component 135 and a component measuring device 137 is obtained, as shown in block 402. Component positioning device 100, 200 includes a first support device 102, 202, a second support device 104, 204 and an adapter device 106, 206. Additionally, component 135 includes a component head 178 and a component base 180 and component measuring device 137 includes a first arbor 182 and a second arbor 184. First support device 102, 202 is connected to first arbor 182 and adapter device 106, 206 is connected to second arbor 184, as shown in block 404. Connecting first support device 102, 202 to first arbor 182 may be accomplished by positioning first support device 102, 202 such that first arbor 182 is disposed within first arbor cavity 130, 230. A threaded mounting screw 134, 234 is disposed within first fastening cavity 132, 232 and rotated to threadingly interact with threaded portion 133, 233 of first fastening cavity 132, 232. Threaded mounting screw 134 is rotated until threaded mounting screw 134 fasteningly interacts with first arbor 182.

Similarly, connecting adapter device 106, 206 to second arbor 184 may be accomplished by positioning adapter device 106, 206 such that second arbor is disposed within adapter arbor cavity 176. An additional threaded mounting screw 134 is disposed within adapter fastening cavity 174 and rotated to threadingly interact with threaded portion 133 of adapter fastening cavity 174. Threaded mounting screw 134 is rotated until threaded mounting screw 134 fasteningly interacts with second arbor 184. Second support device 104, 204 is associated with adapter device 106, 206, as shown in block 406. This may be accomplished by positioning second support device 104, 204 within adapter device cavity 172 so stabilizing member 160, 260 protrudes out of and away from adapter device cavity 172. This configuration positions first support device 102, 202 in proximity with second support device 104, 204 such that first support device 102, 202 is separated from second support device 104, 204 by a component cavity 186.

Component 135 is positioned within component positioning device 100, 200 so that component head 178 is disposed within first component cradle 118, 218 of first support device 102, 202 and/or so that component base 180 is disposed within second component cradle 146, 246 of second support device 104, 204, as shown in block 408. At least one of first arbor 182 and second arbor 184 is then moved toward the other of first arbor 182 and second arbor 184 to reduce the size of the component cavity 186 between first arbor 182 and second arbor 184.

It should be appreciated that component base 180 is disposed within second component cradle 146, 246 of second support device 104, 204 such that only the first incomplete thread is buried and that all of the full threads are not disposed within component cradle 146, 246. This exposes the full threads to the component measuring device 137 to allow component measuring device 137 to measure predetermined characteristics of a component.

Referring to FIGS. 17, 24-27 a block diagram illustrating a method 400 for implementing a component positioning device 300 is shown and discussed. A component positioning device 300, a component 135 and a component measuring device 137 is obtained, as shown in block 402. Although component 135 is shown as a t-shaped component, component 135 may be any shaped component suitable to the desired end purpose, such as an elbow shaped component. Component positioning device 300 includes a first support device 302, a second support device 304, 204, 104 and an adapter device 306 206, 106. Additionally, component 135 is shown as being a "T-shaped" component having a component head 378 and a component base 380 and component measuring device 137 includes a first arbor 182 and a second arbor 184. First support device 302 is connected to first arbor 182 and adapter device 306, 206, 106 is connected to second arbor 184, as shown in block 504. Connecting first support device 302 to first arbor 182 may be accomplished by positioning first support device 302 such that first arbor 182 is disposed within first arbor cavity 330. A threaded mounting screw 134 is disposed within first fastening cavity 332 and rotated to threadingly interact with threaded portion 133 of first fastening cavity 332. Threaded mounting screw 134 is rotated until threaded mounting screw 134 fasteningly interacts with first arbor 182.

Similarly, connecting adapter device 306, 206, 106 to second arbor 184 may be accomplished by positioning adapter device 306, 206, 106 such that second arbor is disposed within adapter arbor cavity 176. An additional threaded mounting screw 134 is disposed within adapter fastening cavity 174 and rotated to threadingly interact with threaded portion 133 of adapter fastening cavity 174. Threaded mounting screw 134 is rotated until threaded mounting screw 134 fasteningly interacts with second arbor 184. Second support device 304, 204, 104 is associated with adapter device 306, 206, 106, as shown in block 506. This may be accomplished by positioning second support device 304, 204, 104 within adapter device cavity 172 so stabilizing member 160, 260 protrudes out of and away from adapter device cavity 172. This configuration positions first support device 302 in proximity with second support device 304, 204, 104 such that first support device 302 is separated from second support device 304, 204, 104 by a component cavity 186.

Component 135 is positioned within component positioning device 300 so that component head 178 is disposed within first component cradle 318 and so that component base 180 is disposed within second component cradle 246, 146 as shown in block 408. At least one of first arbor 182 and second arbor 184 is moved toward the other of first arbor 182 and second arbor 184 to reduce the size of component cavity 186 between first arbor 182 and second arbor 184 such that component 135 is stably disposed between first arbor 182 and second arbor 184.

It should be appreciated that component base 180 is disposed within second component cradle 146, 246 of second support device 104, 204 such that only the first incomplete thread is buried and that all of the full threads are not disposed within component cradle 146, 246. This exposes the full threads to the component measuring device 137 to allow component measuring device 137 to measure predetermined characteristics of component 135.

Figure 17:
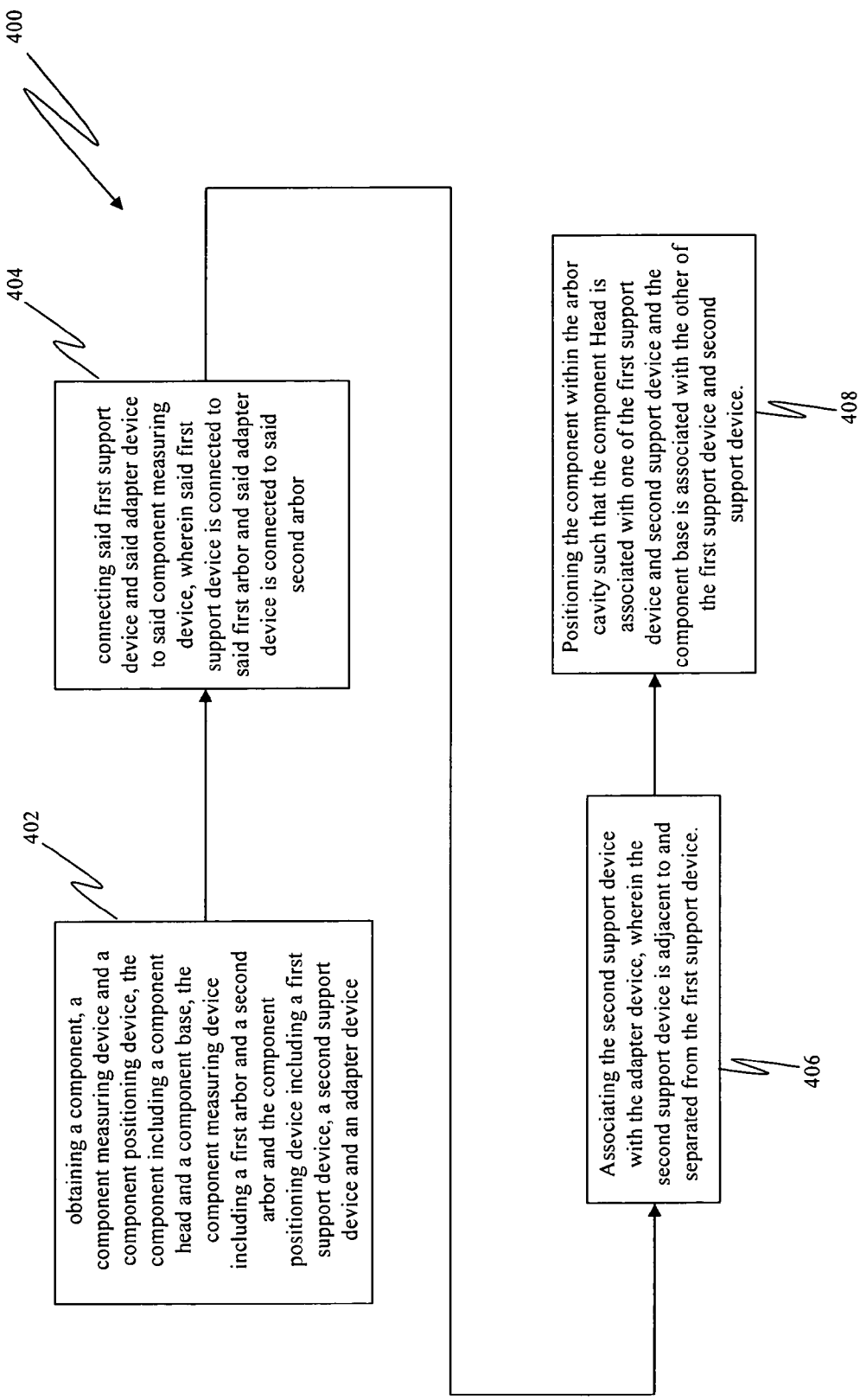
FIG. 17 is a block diagram illustrating a method for implementing a component positioning device.
Figure 18:
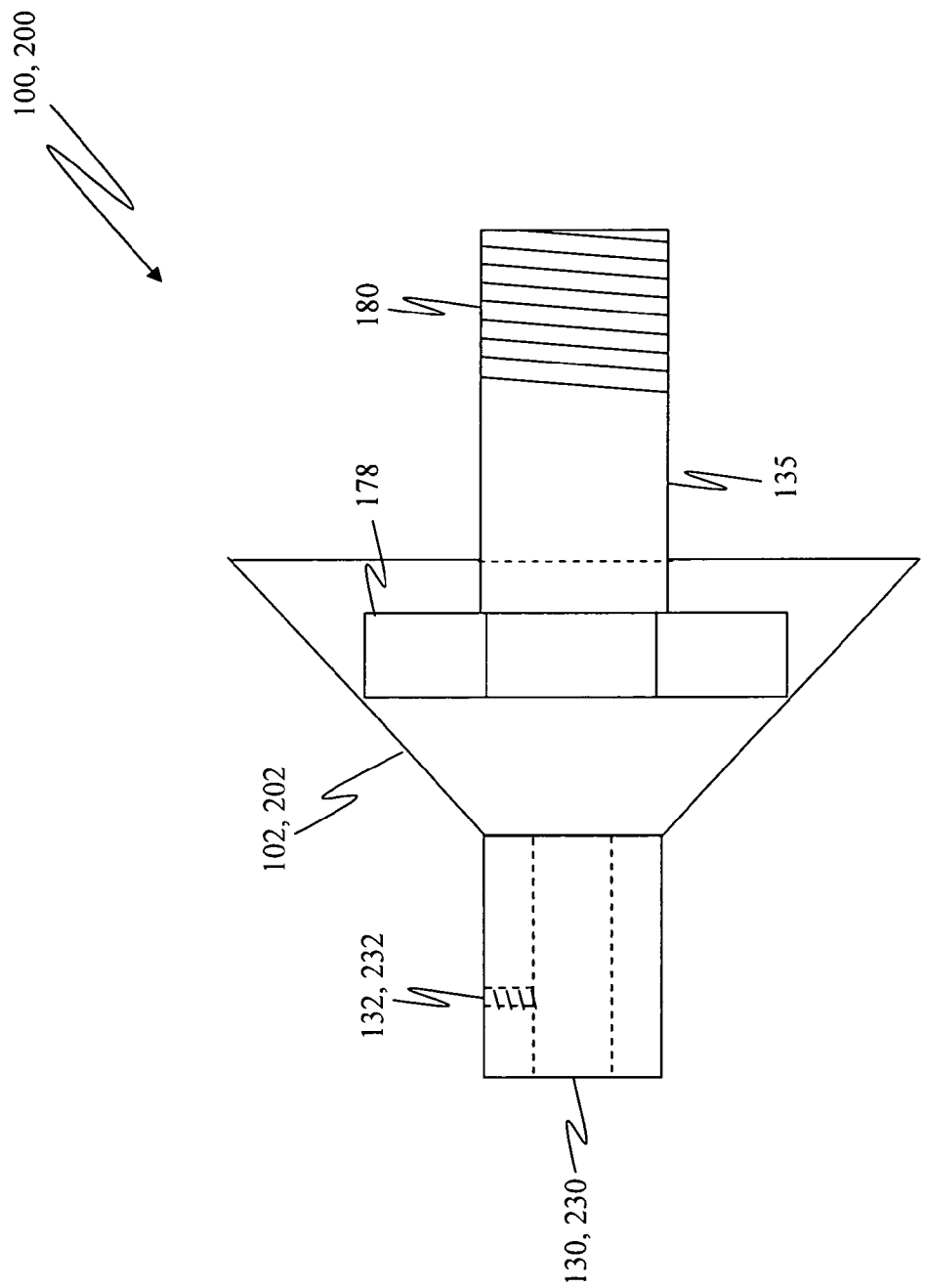
FIG. 18 shows a screw component associated with a first support device.
Figure 19:
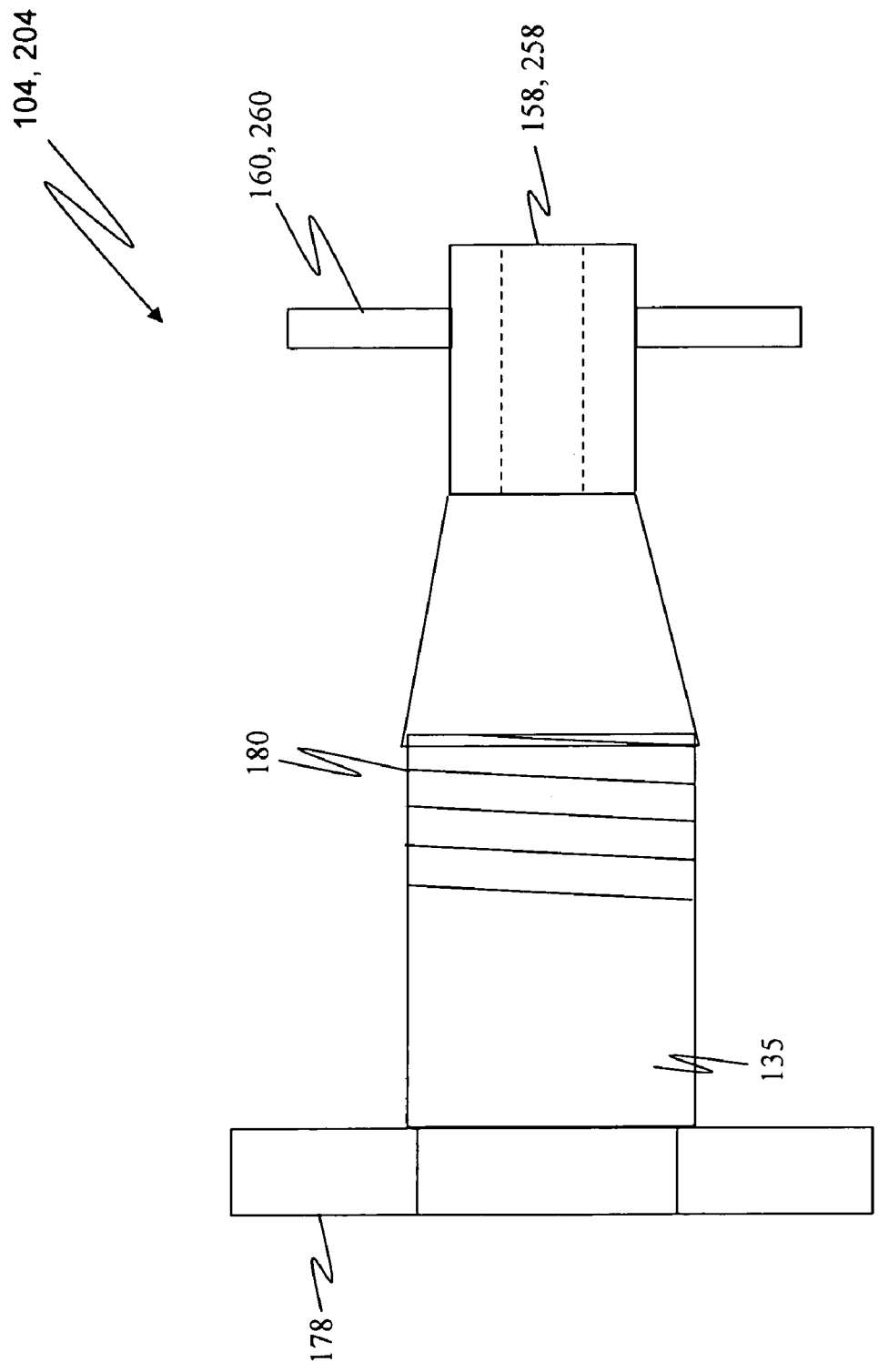
FIG. 19 shows a screw component associated with a second support device.
Figure 20:
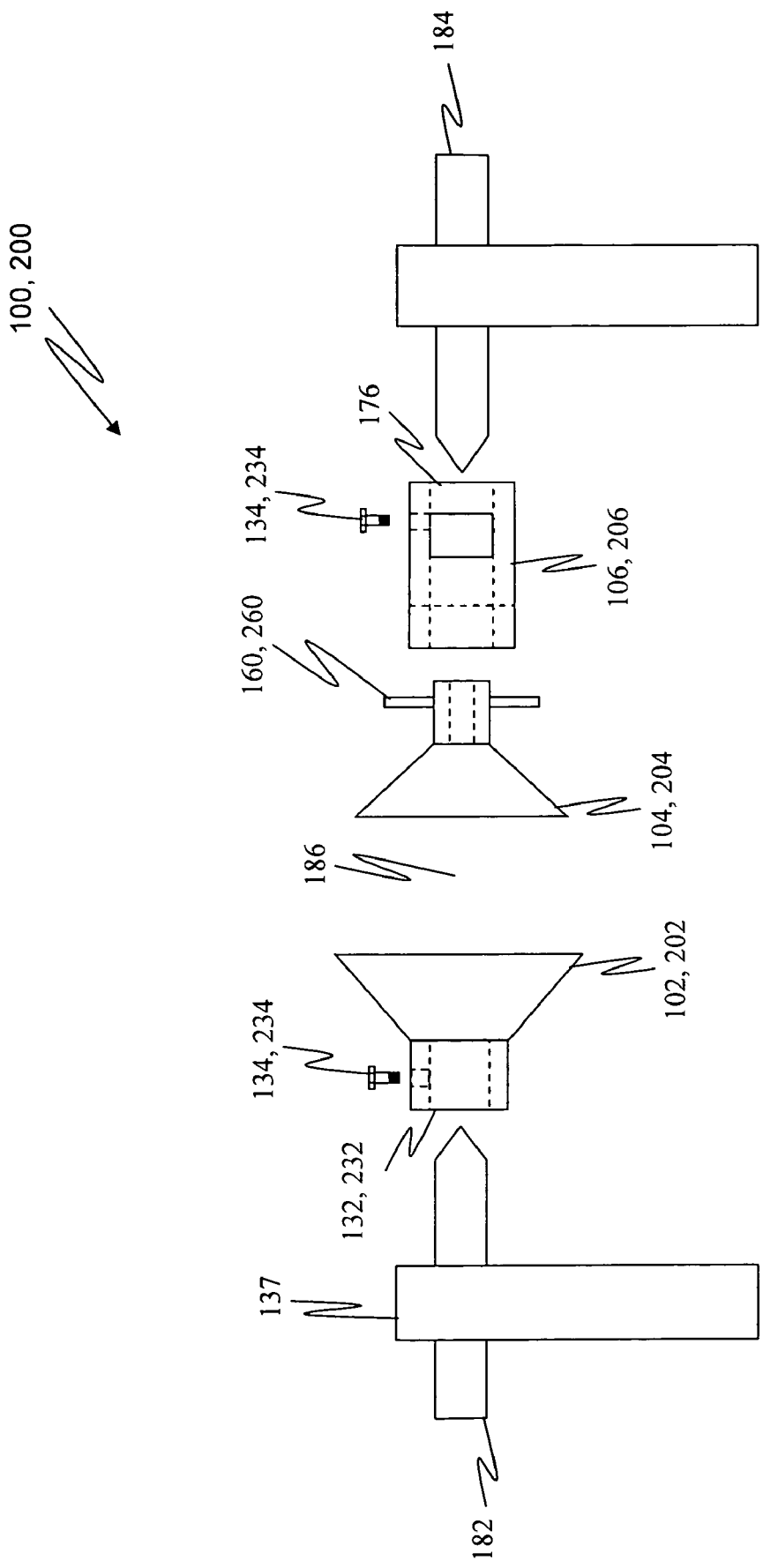
FIG. 20 is an exploded side view of a component support device associated with a component measuring system.
Figure 21:
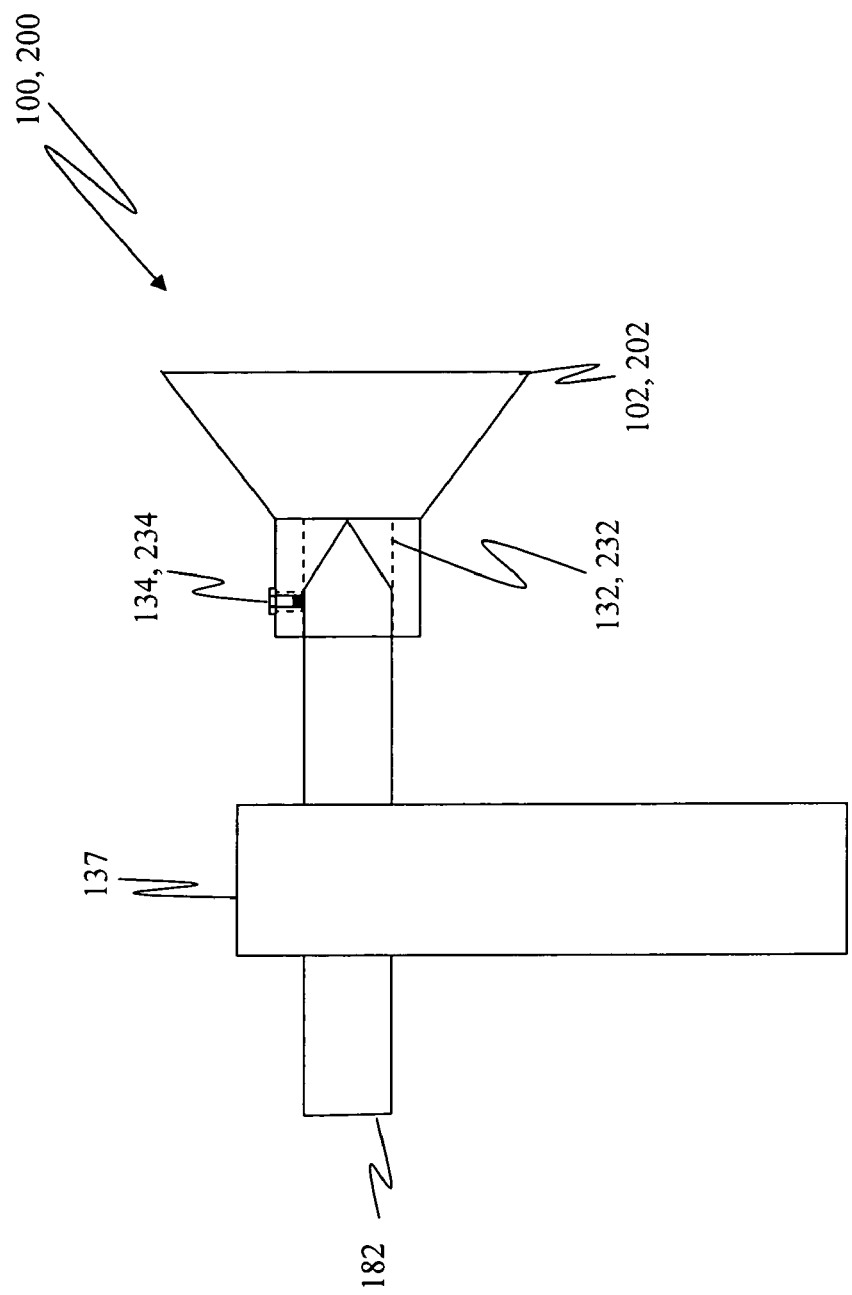
FIG. 21 is a cross sectional side view of a first support device associated with an arbor of a component measuring system.
Figure 22:
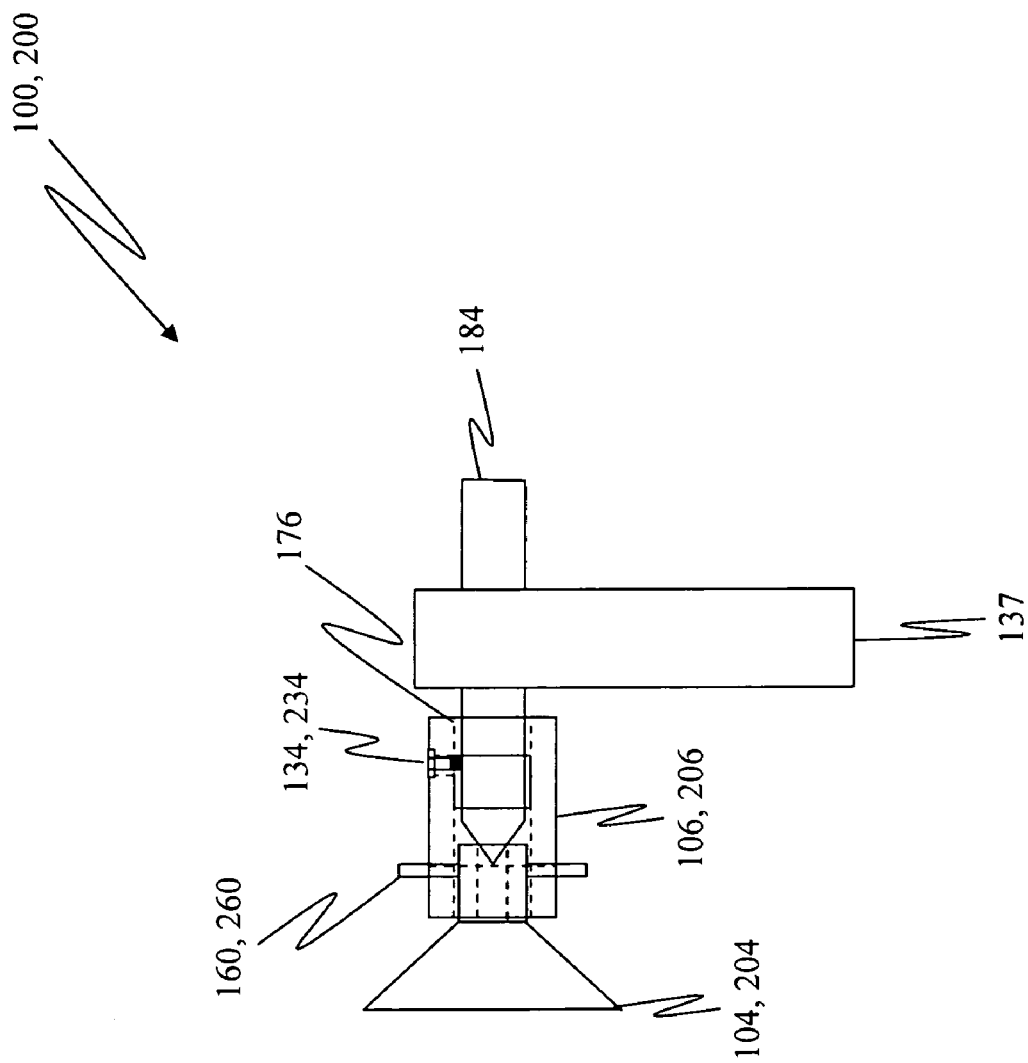
FIG. 22 is a cross sectional side view of a second support device associated with an arbor component measuring system.
Figure 23:
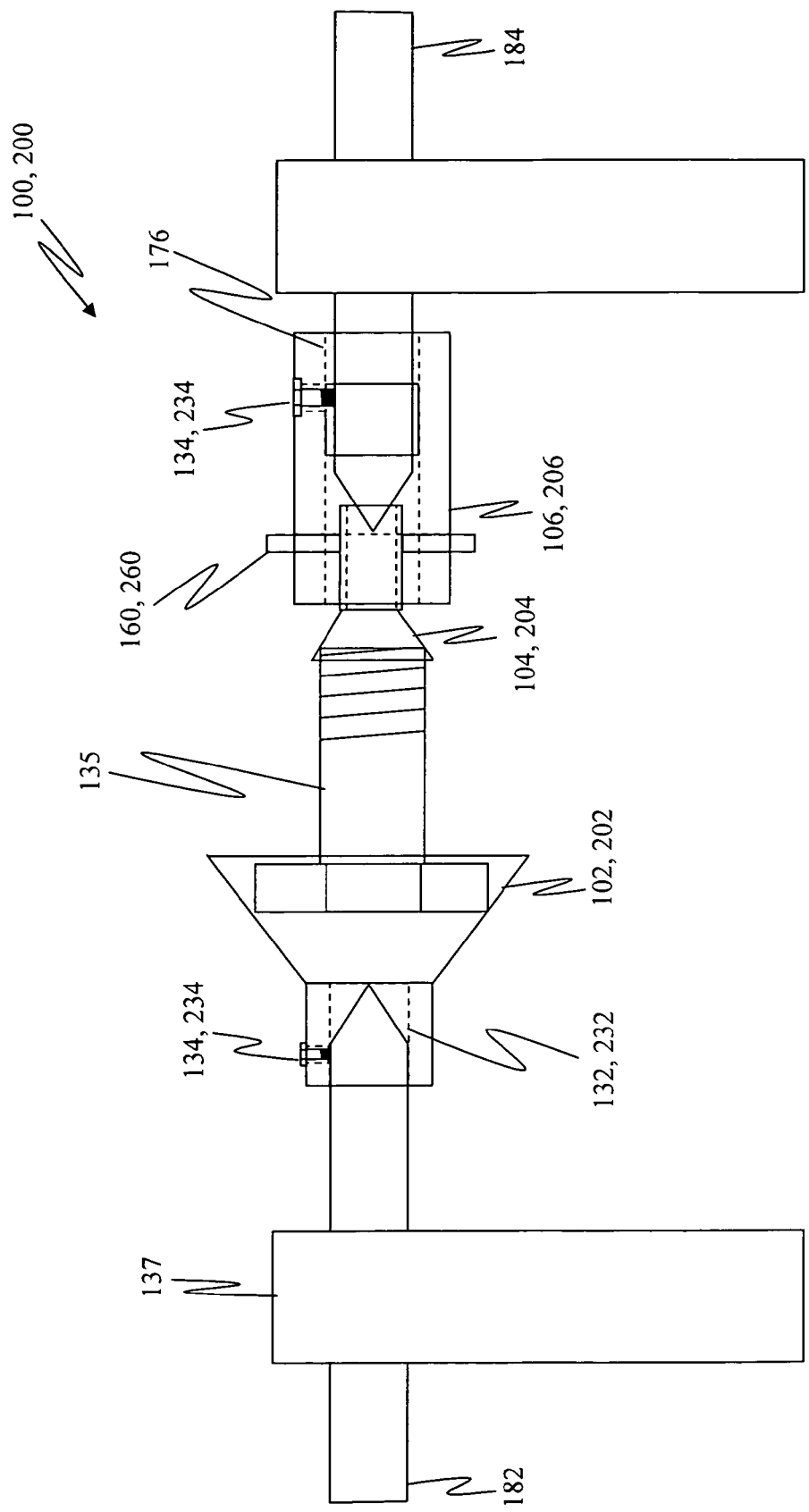
FIG. 23 is a cross sectional side view of a screw component associated with a component support device.
Figure 24:
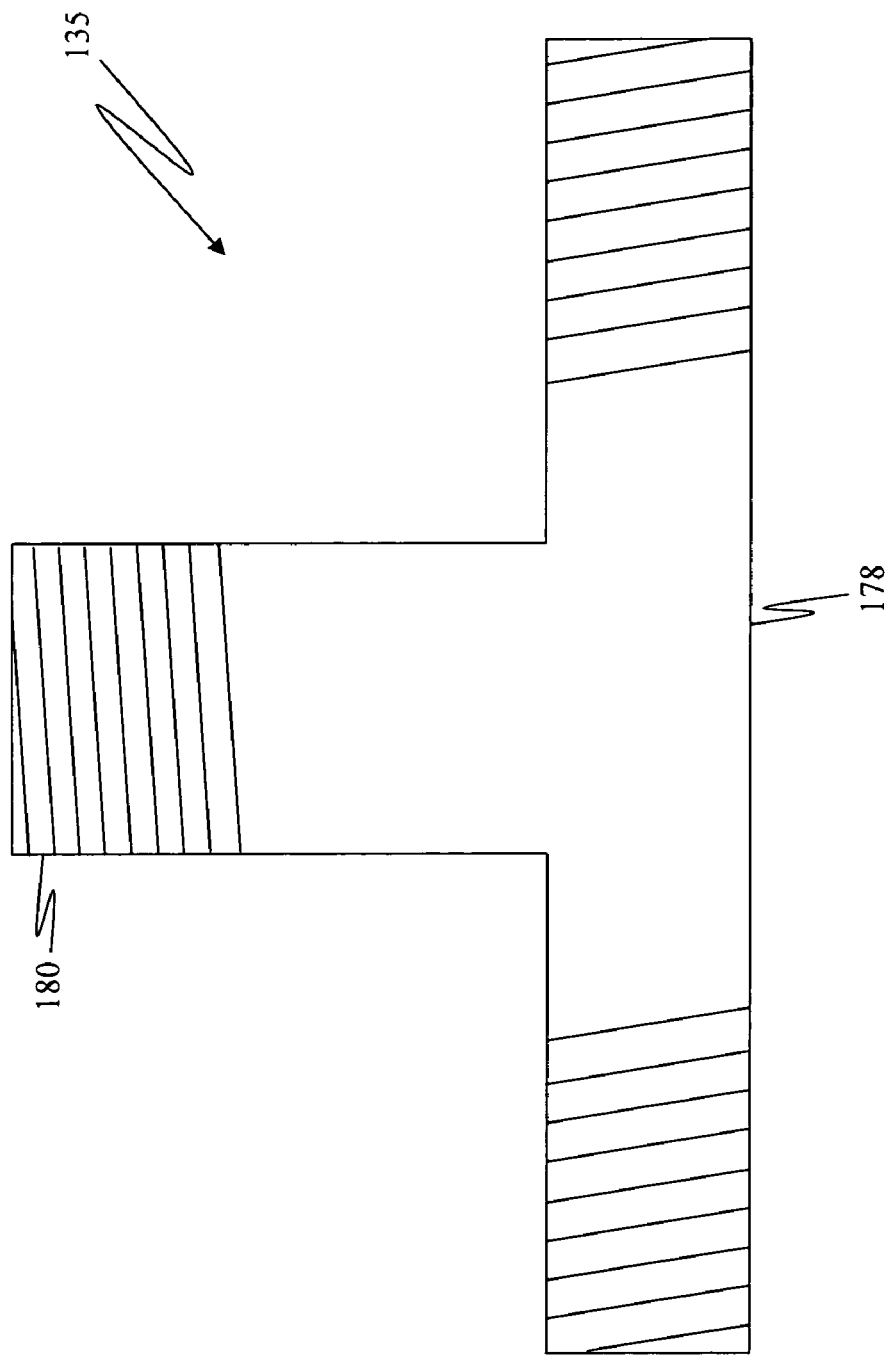
FIG. 24 is a side view of a three sectional screw component to be measured.
Figure 25:
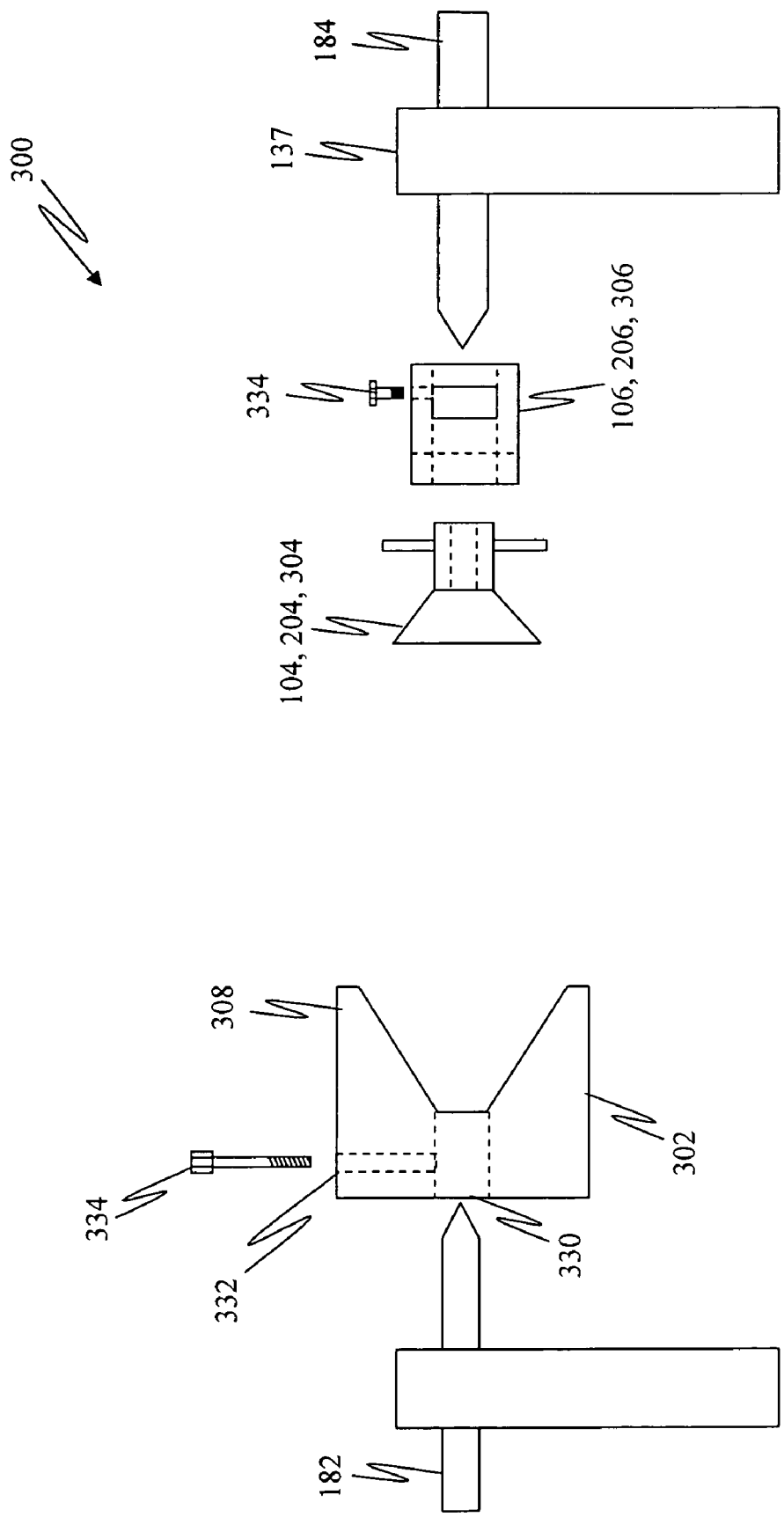
FIG. 25 is a side view of a component support device, in accordance with a third embodiment.
Figure 26:
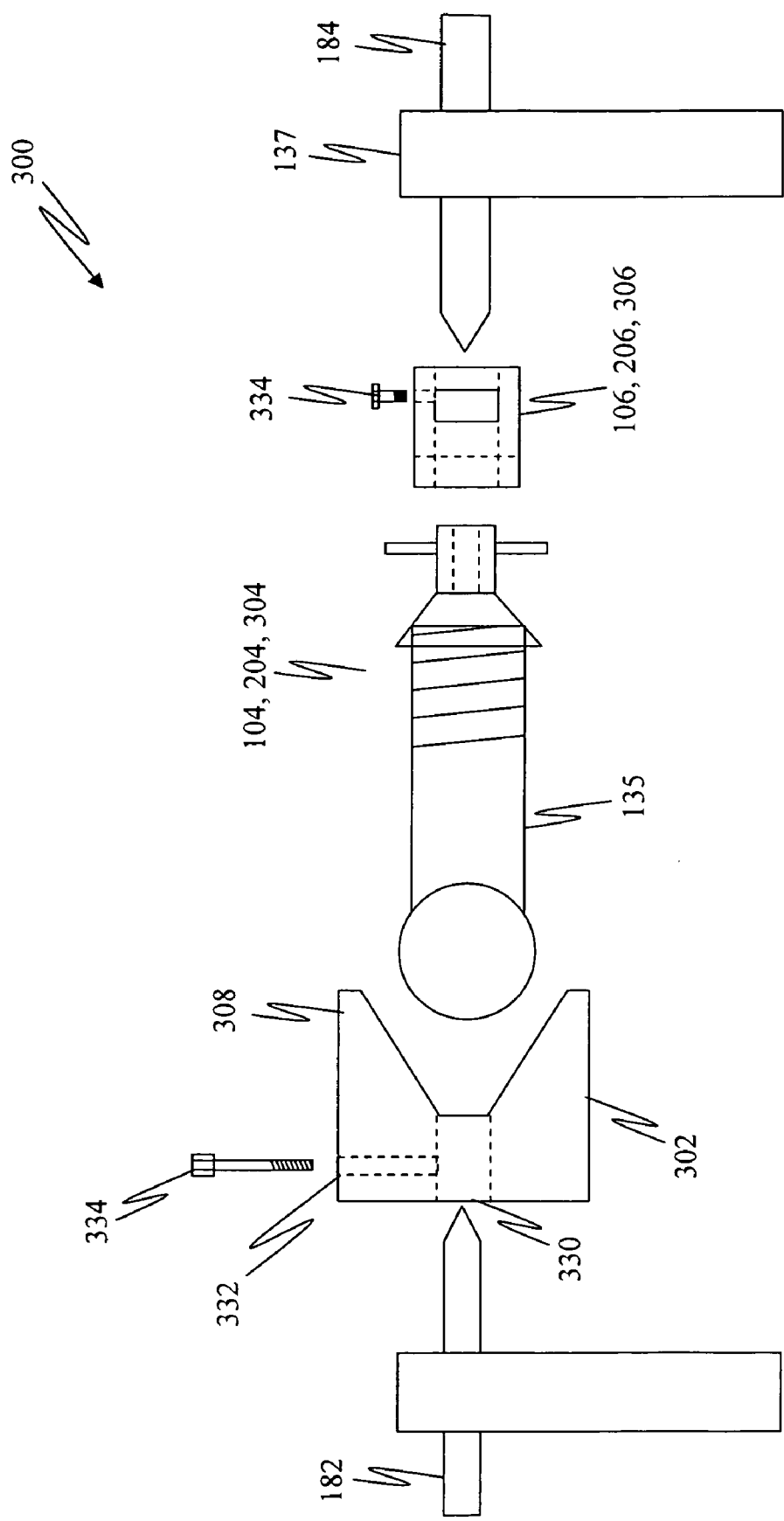
FIG. 26 is an exploded side view of the component support device of FIG. 25 associated with a component measuring system.
Figure 27:
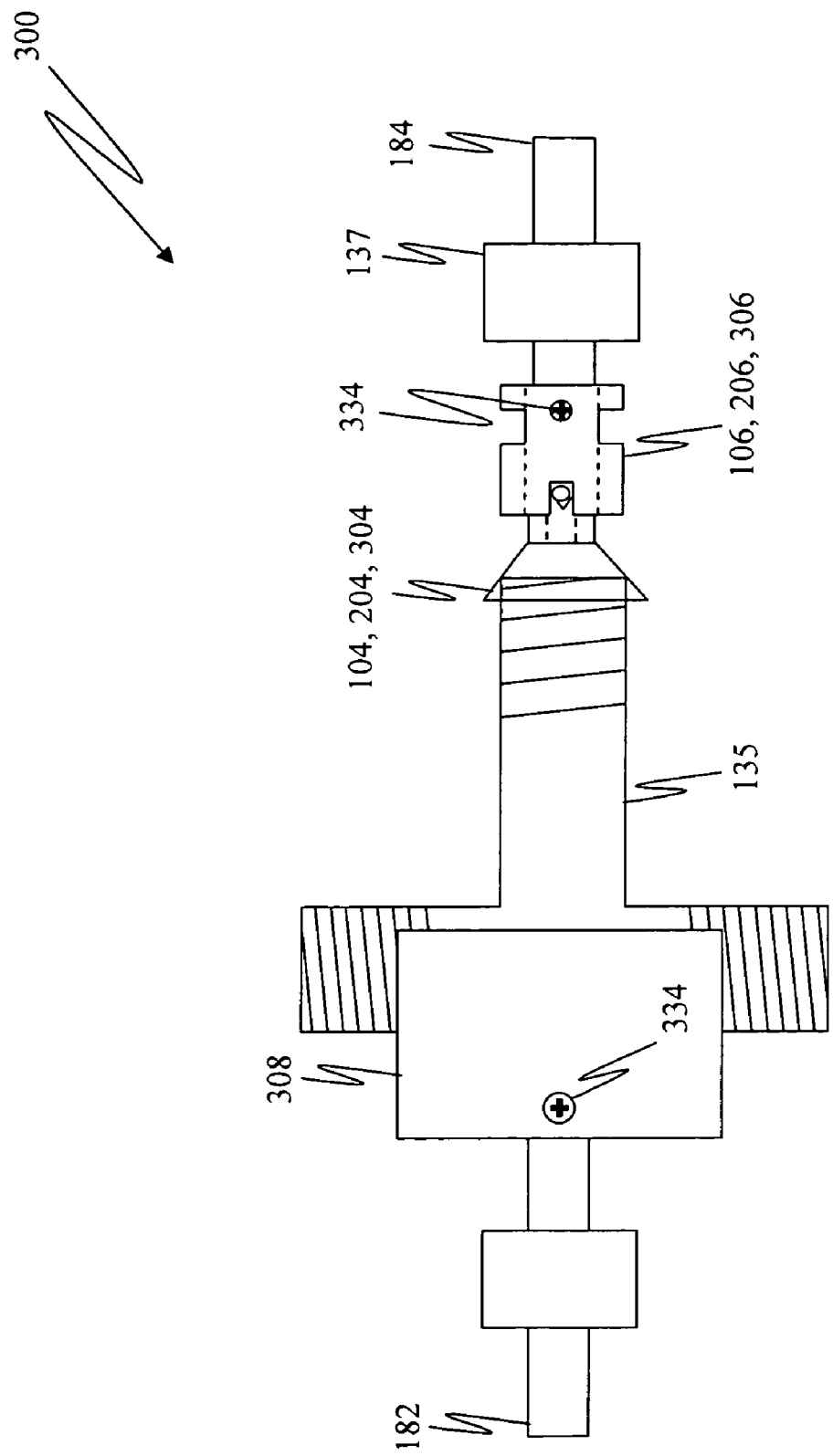
FIG. 27 is a cross sectional top down view of a three sectional screw component associated with the component support device of FIG. 25.

In accordance with an exemplary embodiment, the processing of at least a portion of the method in FIG. 17 may be implemented by a controller disposed internal, external or internally and externally to a component positioning device 100, 200, 300. In addition, processing of at least a portion of the method in FIG. 17 may be implemented through a controller operating in response to a computer program. In order to perform the prescribed functions and desired processing, as well as the computations therefore (e.g. execution control algorithm(s), the control processes prescribed herein, and the like), the controller may includes, but not be limited to, a processor(s), computer(s), memory, storage, register(s), timing, interrupt(s), communication interface(s), and input/output signal interface(s), as well as combination comprising at least one of the foregoing.

The invention may be embodied in the form of a computer or controller implemented processes. The invention may also be embodied in the form of computer program code containing instructions embodied in tangible media, such as floppy diskettes, CD-ROMs, hard drives, and/or any other computer-readable medium, wherein when the computer program code is loaded into and executed by a computer or controller, the computer or controller becomes an apparatus for practicing the invention. The invention can also be embodied in the form of computer program code, for example, whether stored in a storage medium, loaded into and/or executed by a computer or controller, or transmitted over some transmission medium, such as over electrical wiring or cabling, through fiber optics, or via electromagnetic radiation, wherein when the computer program code is loaded into and executed by a computer or a controller, the computer or controller becomes an apparatus for practicing the invention. When implemented on a generalpurpose microprocessor the computer program code segments may configure the microprocessor to create specific logic circuits.

An exemplary embodiment is described herein by way of illustration as may be applied to the positioning of various types of threaded gages, screws, bolts and other components into an inspection system for inspection. While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment disclosed as the best mode contemplated for carrying out this invention

What is claimed is:

1. A method for implementing a component positioning device, comprising:
   obtaining a component, a component measuring device and a component positioning device, said component including a component head and a component base, said component measuring device including a first arbor and a second arbor and said component positioning device including a first support device, a second support device and an adapter device;
   connecting said first support device and said adapter device to said component measuring device, wherein said first support device is associated with said first arbor and said adapter device is associated with said second arbor;
   associating said second support device with said adapter device, wherein said second support device is adjacent to and separated from said first support device by a component cavity; and
   positioning said component within said component cavity such that said component head is associated with one of said first support device and said second support device and said component base is associated with the other of said first support device and said second support device.

2. The method of claim 1, wherein said connecting includes connecting said first support device to said first arbor using a threaded mounting screw.

3. The method of claim 1, wherein said connecting includes connecting said adapter to said second arbor using a threaded mounted screw.

4. The method of claim 1, wherein said adapter device includes an adapter device cavity and wherein said associating includes disposing said second support device within said adapter device cavity.

5. The method of claim 4, wherein said adapter device includes at least one adapter notch cavity and said second support device includes at least one protruding stabilizing member.

6. The method of claim 5, wherein said associating includes disposing said second support device within said adapter device cavity so that said at least one protruding stabilizing member is disposed within said at least one adapter notch cavity.

7. The method of claim 1, wherein said first support device includes a first component cradle and wherein said positioning includes associating said component head with said first component cradle.

8. The method of claim 1, wherein said second support device includes a second component cradle and wherein said positioning includes associating said component base with said second component cradle.

* * * * *